United States Patent
Kelley et al.

(10) Patent No.: US 6,440,965 B1
(45) Date of Patent: Aug. 27, 2002

(54) SUBSTITUTED PYRIMIDINE DERIVATIVES, THEIR PREPARATION AND THEIR USE IN THE TREATMENT OF NEURODEGENERATIVE OR NEUROLOGICAL DISORDERS OF THE CENTRAL NERVOUS SYSTEM

(75) Inventors: James L. Kelley, Raleigh; Thomas A. Krenitsky, Chapel Hill; Lilia M. Beauchamp, Raleigh, all of NC (US)

(73) Assignee: Krenitsky Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 09/529,559

(22) PCT Filed: Jan. 13, 1998

(86) PCT No.: PCT/US98/21517

§ 371 (c)(1),
(2), (4) Date: Apr. 14, 2000

(87) PCT Pub. No.: WO99/19305

PCT Pub. Date: Apr. 22, 1999

Related U.S. Application Data

(60) Provisional application No. 60/062,339, filed on Oct. 15, 1997.

(51) Int. Cl.$^7$ .................... C07D 239/48; C07D 401/04; C07D 239/42; A61K 31/505
(52) U.S. Cl. .................... 514/232.2; 544/298; 544/123; 544/295; 514/252.2; 514/235.8; 514/272; 514/252.18
(58) Field of Search ................................ 544/298, 123, 544/295; 514/252.2, 235.8, 272, 252.18, 232.2

(56) References Cited

U.S. PATENT DOCUMENTS

| | | | |
|---|---|---|---|
| 2,691,655 A | 10/1954 | Hitchings et al. | |
| 3,154,551 A | 10/1964 | Hitchings et al. | ......... 260/256.5 |
| 5,075,305 A | 12/1991 | Hobbs et al. | ............. 514/235.8 |
| 5,525,604 A | 6/1996 | Lee et al. | .................... 514/256 |

FOREIGN PATENT DOCUMENTS

| | | |
|---|---|---|
| DE | 23 44 611 A | 3/1974 |
| DE | 25 33 710 A | 2/1976 |
| DE | 42 39 440 A | 6/1993 |
| EP | 0 372 934 | 6/1990 |
| EP | 0 459 819 A | 12/1991 |
| EP | 0 465 323 A | 1/1992 |
| EP | 0 640 599 | 3/1995 |
| EP | 0826 674 A | 3/1998 |
| JP | 08 283246 A | 10/1996 |
| WO | WO92/18498 | 10/1992 |
| WO | WO93 08169 A | 4/1993 |
| WO | WO94/14780 | 7/1994 |
| WO | WO96 31488 A | 10/1996 |
| WO | WO99 19305 A | 4/1999 |

OTHER PUBLICATIONS

Lehmann, et al, "Neurite Outgrowth of Neurons of Rat Dorsal Root Ganglia Induced by New Neurotrophic Substances With Guanidine Group", Neuroscience Letters, 1993, pp. 57–60, Elsevier Scientific Publishers Ireland, Ltd. vol. 152.

Awaya, et al. "Neurotrophic Pyrimidine Heterocycle Compounds. I. The Newly Synthesized Pyrimidine Compounds Promote Neurite Outgrowth of GOTO and Neuro 2a Neuroblastoma Cell Lines, and Potentiate Nerve Growth Factor (NGF)–Induced Neurite Sprouting of PC 12 Cells", Biol. Pharm. Bull., 1993, pp248–253, Pharmaceutical Society of Japan, vol. 16(3).

Beilstein, CA Abstract No. 6328–42–3.

Roth, et al. "5–Arylthiopyrimidines. II. 2– and 4–Alkylamino and 4–Amino Derivatives", *J. Org. Chem.*, 1961, pp. 2770–2778, vol. 26.

Falco, et al. "5–Arylthiopyrimidines. I. 2, 4–Diamino Derivatives", *J. Org. Chem.*, 1961, pp. 1143–1146, vol. 26.

Hull, et al. "70. Synthetic antimalarials. Part III. Some derviatives of mono– and di–alkylpyrimidines", *J. Chem. Soc.*, 1946, pp. 357–362.

Curd, et al. "74. Synthetic antimalarials. Part VII. 2–Arylamino–4–dialkylaminoalkylaminopyrimidines. Variation of substituents in the 5– and 6–position" *J. Chem. Soc.*, 1946, pp.378–384.

Hull, et al. "9. Synthetic antimalarials. Part XI. The effect of variation of substituents in derviatives of mono– and di–alkylpyrimidines" *J. Chem. Soc.*, 1947, pp. 41–52.

Roth, et al. "5–Benzyl–2,4–diaminopyrimides as antibacterial agents. I. Synthesis and antibacterial activity in vitro" *J. Med. Pharm. Chem,.*, 1962, pp. 1103–1123, vol. 5.

Aroyan, et al., "Synthesis and some reactions of 4–hydroxy–5–(p–alkoxybenzyl)–6–methyl–2–mercapto– (and 2–amino–)pyrimidines" *Chemical Abstracts*, 1968, p. 1241, vol. 68, No. 3.

Aroyan, et al., "Pyrimidine derivatives. X. Synthesis of amino and hydrazino derivatives of 2–(methylthio)–5–(p–alkoxybenzyl)–6–methyl pyrimidines, and a study of their antineoplastic activity", *Chemical Abstracts*, 1969, p. 347, vol. 71, No. 21.

Kramer, et al., "Pyrimidine derivatives. XVI. 4–(p–Alkoxyphenyl)–2, 6–dimethyl–4–pyrimidinylaminophosphonic diaziridides", *Chemical Abstracts*, 1970, p. 326, vol. 73, No. 7.

(List continued on next page.)

Primary Examiner—Mukand J. Shah
Assistant Examiner—Hang Liu
(74) Attorney, Agent, or Firm—Alston & Bird LLP

(57) ABSTRACT

The present invention relates to novel derivatives of a series of substituted pyrimidines, to pharmaceutical compositions which contain them, to methods for their preparation and to their use in therapy, particularly in the treatment of neurodegenerative or other neurological disorders of the central and peripheral systems.

18 Claims, No Drawings

OTHER PUBLICATIONS

Aroyan, et al., "Pyrimidine derivaties. XXXV. Synthesis of 2, 4–bis(arylamino)– and 2, 4–bis(aryloxy)–5–(p–alkoxybenzyl)–6–methoylpyrimidines", *Chemical Abstracts*, 1975, p. 601, vol. 82, No. 23.

Aroyan, et al., "Pyrimidine derivaties. XLIV. Synthesis and reactions of 2–phenyl–4–hydroxy–5–(p–alkoxybenzyl)–6–methylpyrimidines", *Chemical Abstracts*, 1976, p. 515, vol. 84, No. 9.

Ordukhanyan, et al., "Study of the relation between structure and biological activity. II. Antineoplastic activity of pyrimidine derivatives", *Chemical Abstracts*, 1980, p. 25, vol. 92, No. 3.

Goldberg, A., "No. 218. Préparation de quelques 5–benzyl pyrimidines" *Bulletin De La Societe Chimique France*, 1951, pp. 895–899.

E.A. Coats et al., "Correlation Analysis of Pyrimidines Folic Acid Antagonist as Antibacterial Agents.I.", *Euro. J. Med. Chem.—Chemica Therapeutica*, May 1979, pp. 261–270, vol. 14, No. 3, Editions Scientifique Elsevier,Paris.

Chemical Abstracts 1997, p. 620, col. 2, vol. 126, No. 7, abstract No. 89387X.

U.S. application No. 09/288,495, filed Apr. 8, 1999, Kelley et al.

Smano, et al., "An Improved Synthesis of 2–Amino–5–[(4–chlorophenyl)thio]–4–morpholinopyrimidine (BW 394U)—A Potential Antisenility Agent", *J. Heterocyclic Chem.*, Jan.–Feb. 2000, pp. 183–185, vol. 37.

Vaillancourt, et al., "Synthesis and Self–Association of 4–Pyrimidines", *J. Org. Chem.*, 1998, pp. 9746–9752, vol. 63, No. 26.

SUBSTITUTED PYRIMIDINE DERIVATIVES, THEIR PREPARATION AND THEIR USE IN THE TREATMENT OF NEURODEGENERATIVE OR NEUROLOGICAL DISORDERS OF THE CENTRAL NERVOUS SYSTEM

This application claims the benefit of U.S. Provisional Application No. 60/062,339, filed on Oct. 15, 1997.

BACKGROUND OF THE INVENTION

The present invention relates to novel derivatives of a series of substituted pyrimidines, to pharmaceutical compositions which contain them, to methods for their preparation and to their use in therapy, particularly in the treatment of neurodegenerative or other neurological disorders of the central and peripheral systems.

Dementing disorders such as age-related cognitive disorders, e.g., senility or Alzheimer's disease are medical conditions for which there are currently only limited therapies. Although studies suggest that multiple neurotransmitter systems are involved in senile dementia, a loss of cholinergic neurons and a severe depletion of choline acetyltransferase appear to show the earliest and strongest correlations with functional cognitive impairment [see P. T. Francis, A. M. Palmer, N. R. Sims, D. M. Bowen, A. N. Davison, M. M. Esiri, D. Neary, J. S. Snowden and G. K. Wilcock, Neurochemical Studies of Early-onset Alzheimer's Disease. N. Engl. J. Med., 313, 7 (1985); R. T. Bartus, R. L. Dean, M. Pontecorvo and C. Flicker, The Cholinergic Hypothesis: A Historical Overview, Current Perspective, and Future Directions. Ann. N. Y. Acad. Sci., 444, 332 (1985); F. Hefti and L. S. Schneider, Nerve Growth Factor and Alzheimer's Disease, Clin. Neuropharmacol., 14, S62 (1991)]. Several groups have attempted to stimulate cholinergic activity by blocking the breakdown of acetylcholine with acetylcholine esterase inhibitors or by introducing muscarinic or nicotinic agonists [see R. T. Bartus, R. L. Dean III, B. Beer and A. S. Lippa, The Cholinergic Hypothesis of Geriatric Memory Dysfunction. Science, 217, 408 (1982); J. Varghese, I. Lieberburg and E. D. Thorsett, Chapter 21. Alzheimer's Disease: Current Therapeutic Approaches. Annu. Rep. Med. Chem., 28, 197 (1993)]. The approved drugs Cognex® and Aricept® are acetylcholine esterase inhibitors.

Nerve growth factor (NGF) is the best characterized neurotropic factor that is capable of inducing cell differentiation of neural cells and promoting neurite sprouting. The neurotrophic protein NGF primarily affects cholinergic neurons in the central nervous system and may be necessary for their survival [see F. Hefti and P. A. Lapchak, Pharmacology of Nerve Growth Factor in the Brain. Adv. Pharmacol., 24, 239 (1993)]. NGF is not systemically bioavailable, but if it is injected or infused directly into brain, it prevents neuronal cell loss and restores cognitive function in aged or lesioned rats or monkeys [see W. Fischer, A. Bjorklund, K. Chen and F. H. Gage, NGF Improves Spatial Memory in Aged Rodents as a Function of Age. J. Neurosci., 11, 1889 (1991)]. NGF effects ultimately result in the stimulation of choline acetyltransferase, the enzyme for biosynthesis of acetylcholine and the promotion of neurite growth. Consequently, small molecules that produce neurotrophic or "nerve growth factor-like" (NGF-like) properties in mammalian cell cultures have potential for use in the treatment of dementing disorders such as age-related senility or Alzheimer's disease and other neurodegenerative conditions such as peripheral neuropathies, Parkinson's, stroke damage, transient ischemic attacks or trauma-head injuries.

There are several reports of small molecules that exhibit various aspects of NGF-like activity. Isaxonine [2-(isopropylamino)pyrimidine] was developed as a neurotrophic pharmaceutical but the clinical application was withdrawn, possibly due to toxicological effects [see Neuropathies peripheriques et a l'isaxonine. Nouv. Presse Med., 11, 1189 (1982); S. Lehmann, C. Quirosa-Guillou, U. Becherer, C. Thai and J.-P. Zanetta, Neurite Outgrowth of Neurons of Rat Dorsal Root Ganglia Induced by New Neurotrophic Substances with Guanidine Group. Neurosci. Lett., 152, 57 (1993)]. Several 2-(piperazino)pyrimidine derivatives were reported to possess NGF-like activity and are being studied further for use in treating CNS degenerative diseases [see A. Awaya, H. Kobayashi, K. Horikomi, S. Tanaka, A. M. Kabir, K. Yokoyama, H. Ohna, K. Kato, T. Kitahara, I. Tomino, S. Isayama and S. Nakamura, Neurotrophic Pyrimidine Heterocyclic Compounds. I. The Newly Synthesized Pyrimidine Compounds Promote Neurite Outgrowth of GOTO and Neuro 2a Neuroblastoma Cell Lines, and Potentiate Nerve Growth Factor (NGF)-Induced Neurite Sprouting of PC-12 Cells. Biol. Pharm. Bull., 16, 248 (1993)]. AIT-082 (4[[3-(1,6-dihydro-6-oxo-9-purin-9-yl)-1-oxopropyl]amino]benzoic acid) is reported to enhance NGF action in cultured PC-12 cells and to restore age induced working memory deficits in mice [see P. J. Middlemiss, A. J. Glasky, M. P. Rathbone, E. Werstuik, S. Hindley and J. Gysbers, AIT-082, A Unique Purine Derivitive, Enhances Nerve Growth Factor Mediated Neurite Outgrowth from PC-12 cells, Neuroscience Let., 199, 131 (1995)]. In addition, U.S. Pat. No. 5,075,305 discloses 2-amino-5-bromo-4-(morpholino)pyrimidine as having NGF-like properties and its possible use in treating CNS degenerative diseases like Alzheimer's disease as well as peripheral neuropathies or other peripheral nervous system disorders.

European Patent Applicaton EP 0 626 674 A1 discloses a group of 4-substituted amino-5-substituted phenoxy pyrimidine derivatives and their use as psychotropic drugs. European Patent Application 0 459 819 A2 describes a group of 4-substituted amino-5-substituted phenyl pyrimidine derivatives and their use in the treatment of neurological disorders. Document DE 23 44 611 A discloses a group of 4-substituted amino -5-substituted phenoxy pyrimidine derivatives.

The compound 2-p-chloroanilino-4-β-diethylaminoethylamino-5-phenoxypyrimidine, and its use as antimalarial agent, has been disclosed (See Curd et al., Journal of the Chemical Society, 378–384 (1946). The compounds, 2-amino-4-β-diethylaminoethylamino-5-phenoxypyrimidine and 2-amino-4-γ-diethylaminopropylamino-5-phenoxypyrimidine, and their use as antimalarial agents, have also been disclosed (See Hull et al., Journal of the Chemical Society, 41–52 (1947).

SUMMARY OF THE INVENTION

We have now discovered a series of substituted pyrimidines that demonstrate NGF-like activity and/or enhancement of NGF activity in PC12 cells. The compounds stimulated both neurite outgrowth and choline acetyltransferase activity in In vitro experiments. Such activities are predictive for causing increased choline acetyltransferase activity in rat striatum and improving cognitive performance in animal models of age-induced working memory deficits by potentiating the activity of endogenous NGF in the brain. [P. J. Middlemiss. A. J. Glasky, M. P. Rathbone, E. Werstuik, S. Hindley and J. Gysbers, AIT-082, A Unique Purine Derivitive, Enhances Nerve Growth Factor Mediated Neurite Outgrowth from PC12 cells. Neuroscience Let. 199, 131

(1995); A. J. Glasky, C. L. Melchior, S. Pirzadeh, N. Heydari and R. F. Ritzmannn, Effect of AIT-082, a Purine Analog, on Working Memory in Normal and Aged Mice. Pharmacol. Biochem. Behav., 47, 325 (1994); R. Morris. Developments of a Water-maze Procedure for Studying Spatial Learning in the Rat. J. Neurosci. Methods, 11, 47 (1984)].

DETAILED DESCRIPTION OF THE INVENTION

According to the present invention, there are provided novel compounds of Formula I;

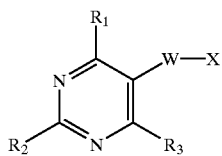

Formula I wherein
W is O, CH2, CH2CH2, OCH2, or CH2CH2CH2;
$R^1$ is hydroxyC1-6alkyamino, morpholino, piperidino, piperazino, piperazinoamino, homopiperazino, homopiperidino, homomorpholino, benzoxazino, indolino, 1,2,3,4-tetrahydroquinolino, benzylamino, wherein C or N atoms may be substituted with one or more substituents selected from the group consisting of:
NR4R5 (wherein R4 and R5 may be the same or different and are H, C1–6alkyl, hydroxyC1–6alkyl, C3–8cycloalkyl, C6–10aryl, C6–10arylCC1–6alkyl, C1–6alkoxy, C6–10aryloxy or C6–10arylC1–6alkoxy);
NR4R5carbonyC1–6alkyl (wherein R4 and R5 may be the same or different);
OH;
CN;
C1–6alkyl;
C2–7alkenyl;
C2–7alkenyl;
C6–10aryl;
C6–10heteroaryl;
hydroxyC1–6alkyl;
dihydroxyC1–6alkyl;
C1–6alkoxy;
C1–6aryloxy;
C6–10heteroaryloxy;
hydroxyC1–6alkoxy;
C1–6alkoxyC1–6alkyl;
C6–10aryloxyC1–6alkyl;
C6–10heteroaryloxyC1–6alkyl;
C3–8cycloalkyl;
C6–10arylC1–6alkyl;
C6–10heteroarylC1–6alkyl;
C6–10arylC1–6alkoxy;
C6–10heteroarylC1–6alkoxy;
C1–6alkylcarbonylC1–6alkyl;
C6–10arylcarbonylC1–6alkyl;
carboxyC1–6alkyl;
C1–6alkoxycarbonylC1–6alkyl;
C6–10aryloxycarbonylC1–6alkyl;
C6–10arylC1–6alkyloxycarbonylC1–6alkyl;
cyanoC1–6alkyl
C1–6alkylthioC1–6alkyl;
C1–6alkylsulfinylC1–6alkyl;
C1–6alkylsulfonylC1–6alkyl;
C6–10arylthioC1–6alkyl;
C6–10arylsulfinylC1–6alkyl;
C6–10arylsulfonylC1–6alkyl;
C6–10arylC1–6alkylthioC1–6alkyl;
C6–10arylC1–6alkylsulfinylC1–6alkyl;
C6–10arylC1–6alkylsulfonylC1–6alkyl;
C6–10heteroarylthioC1–6alkyl;
C6–10heteroarylsulfinylC1–6alkyl;
C6–10heteroarylsulfonylC1–6alkyl;
aziridino;
azetidino;
pyrrolidino;
piperidino;
heptamethyleneimino;
homopiperazino;
N-substituted homopiperazino (wherein the substituent may be C1–6alkyl, C6–10aryl, C6–10arylC1–6alkyl or C6–10heteroaryl);
piperazino;
N-substituted piperazino (wherein the substituent may be C1–6alkyl, C6–10aryl, C6–10arylC1–6alkyl or C6–10heteroaryl);
morpholino;
homomorpholine;
thiomorpholino;
aminoC1–6alkyl;
C1–6alkylaminoC1–6alkyl;
di(C1–6alkyl)aminoC1–6alkyl (wherein the alkyl groups may be the same or different);
C6–10arylaminoC1–6alkyl;
C6–10arylC1–6alkylaminoC1–6alkyl;
di(C6–10aryl)aminoC1–6alkyl (wherein the aryl groups may be the same or different);
di(C6–10arylC1–6alkyl)aminoC1–6alkyl (wherein the arylalkyl groups may be the same or different);
R12C(O)C1–6alkyl (wherein R12 is aziridino, azetidino, pyrrolidino, piperidino, heptamethyleneimino, piperazino, homopiperazino, morpholino, homomorpholino, or thiomorpholino);
C(O)R6; C(O)C(O)R6; C(S)R6; S(O)2R6; and C(NR11)R6 (wherein R11 is hydrogen,
C1–6alkyl or C6–10aryl and R6 may be H or any of the above listed substituents); and
$R^2$ is selected from the group consisting of:
H;
halogen;
N3;
OR;
SR;
C1–6alkyl;
C6–10aryl;
C6–10arylC1–6alkyl;
C6–10heteroaryl;
NR7R8 (wherein R7 and R8 may be the same or different and are H, C1–6alkyl, hydroxyC1–6alkyl, hydroxyC1–6alkyloxyC1–6alkyl; C3–8cycloalkyl, C6–10aryl, C6–10arylC1–6alkyl, C1–6alkoxy, C6–10aryloxy, C6–10arylC1–6alkoxy, C(O)R6, C(O)C(O)R6, C(S)R6, S(O)2R6, or C(NR11)R6);
N=C(R11)N(R6)2;
aziridino;
azetidino;
pyrrolidino;
piperidino;
hydroxypiperidino;
heptamethyleneimino;
piperazino;

N-substituted piperazino (wherein the substituent may be C1–6alkyl, hydroxyC1–6alkyl, C6–10aryl, C6–10arylC1–6alkyl or C6–10heteroaryl);
homopiperazino;
N-substituted homopiperazino (wherein the substituent may be C1–6alkyl, hydroxyC1–6alkyl, C6–10aryl, C6–10arylC1–6alkyl or C6–10heteroaryl);
morpholino;
homomorpholine;
thiomorpholino; and
R12C(O)C1–6alkyl (wherein R12 is aziridino, azetidino, pyrrolidino, piperidino, heptamethyleneimino, piperizino, homopiperazino, morpholino, homomorpholino, or thiomorpholino);
C-substituted piperidino (wherein the substituent is C(O)R6);
C-substituted piperidino (wherein the substituent may be C1–6alkyl, hydroxyC1–6alkyl, C6–10aryl, C6–10arylC1–6alkyl or C6–10heteroaryl);

$R^3$ is H;

X is a C6–10 aryl ring or a C6–10 heteroaryl ring optionally substituted with one or more suitable substituents for an aryl ring; preferably from the group consisting of:
halogen;
C1–6alkyl;
C2–7alkenyl;
C2–7alkynyl;
C6–10aryl;
C6–10heteroaryl;
OR;
NR9R10 (wherein R9 and R10 may be the same or different and are H. C1–6alkyl, C3–8cycloalkyl, C6–10aryl, or C6–10arylC1–6alkyl);
NROR;
C(O)NR9R10;
C(O)OR;
C(O)R;
NRC(O)NR9R10
NRC(O)R;
NRC(O)OR;
CR(OH)R;
OC(O)R;
S(O)nR wherein R is other than H and n is 0, 1 or 2;
NRS(O)mR wherein R is other than H and m is 1 or 2;
S(O)2NR9R10;
NO2;
CN;
CF3; and
OCF3;

R is H, C1–6alkyl, C3–8cycloalkyl, C6–10aryl or C6–10arylC1–6alkyl; provided that when -W-X is benzyl, R1 is not piperidine; and when R1 is a hydroxyalkyloxyalkylamino, R2 is not a heterocyclic ring;

and pharmaceutically acceptable esters, amides, salts or solvates thereof.

The present invention includes all enantiomeric and diastereomeric forms of the compounds of Formula I either individually or admixed in any proportion.

The present invention further includes prodrugs and active metabolites of the compounds of formula I. A prodrug includes any compound which, when administered to a mammal, in converted in whole or in part to a compound of formula I. An active metabolite is a physiologically active compound which results from the metabolism of a compound of formula I, or a prodrug thereof, when such compound or prodrug is administered to a mammal.

The compounds of Formula I above and their pharmaceutically acceptable salts or solvates are sometimes hereinafter referred to as "the compounds according to the invention".

By "alkyl" is meant straight or branched chain alkyl. The alkyl groups may be optionally substituted with hydroxy, amino or halogen.

By "aryl" is meant an aromatic ring such as phenyl or naphthyl;

By "heteroaryl" is meant a ring containing 1 to 4 heteroatoms selected from the group consisting of N, O and S.

By "halogen" is meant F, Cl, Br or I.

Preferred compounds included in the present invention are more particularly defined by the following Formulas IA–ID:

Formula IA

Formula IB

Formula IC

Formula ID wherein a and b are 0 or 1 and a+b=0 or 1 and most preferably a+b=1;

R2 is selected from the group consisting of; NH2, NHC1–6alkyl, NHC2H4OC2H4OC2H4OH,

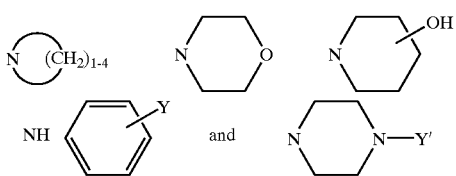

provided that in Formula ID, R2 Is not a hetrocyclic; Y is any suitable substituent for an aryl ring, and Y' is selected from the group consisting of:
H, CH3, CH2CH3, CH2CH2OH, C(O)R, S(O)2R and C6H5,
and pharmaceutically acceptable esters, amides, salts or solvates thereof.

Particularly preferred compounds of Formula I are those wherein W is O, CH2 or CH2CH2 and X is substituted phenyl; and pharmaceutically acceptable salts or solvates thereof.

More preferred compounds of Formula I are those wherein W is O or CH2 and X is substituted phenyl; and pharmaceutically acceptable salts or solvates thereof.

Most preferred compounds of Formula I are those wherein R1 is 4-(2-hydroxyhethyl)piperazino or 2-(2hydroxyethoxy)ethylamino, W is O or CH2, X is substituted phenyl, and R2 is NH2; and pharmaceutically acceptable salts or solvates thereof.

Specifically preferred compounds of Formula I are:
2-Amino-4-morpholino-5-(phenoxy)pyrimidine
2-Amino-5-4-methylphenoxy(morpholino)pyrimidine
2-Amino-5-(4-fluorophenoxy)-4-(morpholino)pyrimidine
2-Amino-5-(4-chlorophenoxy)-4-(morpholino)pyrimidine
2-Amino-5-(4-chlorobenzyloxy)-4-(morpholino)pyrimidine
2-Amino-5-(benzyloxy)-4-(morpholino)pyrimidine
2-Amino-5-(4-chlorophenoxy)-4-(2-(hydroxyethoxy)ethylamino)pyrimidine
2-Amino-4-(4-carbamoylpiperidino)-5-(4-chlorophenoxy)pyrimidine
2-Amino-5-(4-chlorophenoxy)-4-(piperazino)pyrimidine
2-Amino-5-(4-chlorophenoxy)-4-(4-methylpiperazino)pyrimidine
2-Amino-5-(4-chlorophenoxy)-4-(4-ethylpiperazino)pyrimidine
2-Amino-5-(4-chlorophenoxy)-4-(4-(2-hydroxyethyl)piperazino)pyrimidine
2-Amino-5-(4-fluorophenoxy)-4-(4-phenylpiperazino)pyrimidine
2-Amino-5-(4-chlorophenoxy)-4-(4-phenylpiperazino)pyrimidine
2-Amino-5-(4-chlorophenoxy)-4-(4-(2-pyridyl)piperazino)pyrimidine
2-Amino-4-(4-benzylpiperazino)-5-(4-chlorophenoxy)pyrimidine
2-Amino-5-(4-chlorophenoxy)-4-(4-formylpiperazino)pyrimidine
4-(4-Acetylpiperazino)-2-amino-5-(4-chlorophenoxy)pyrimidine
2-Amino-5-(4-chlorophenoxy)-4-(4-methoxyacetylpiperazino)pyrimidine
2-Amino-5-(4-chlorophenoxy)-4-(morpholino)pyrimidine
5-(4-Chlorophenoxy)-2-(dimethylamino)-4-(4-methylpiperazino)pyrimidine
5-(4-Chlorophenoxy)-4-morpholino-2-(3-phenylureido)pyrimidine
5-(4-Chlorophenoxy)-2,4-(dimorpholino)pyrimidine
5-(4-Chlorophenoxy)-2-(4-methylpiperazino)-4-(morpholino)pyrimidine
5-(4-Chlorophenoxy)-4-(4-methylpiperazino)-2-(morpholino)pyrimidine
5-(4-Chlorophenoxy)-4-[4-(2-hydroxyethyl)piperazino]-2-(morpholino)pyrimidine
2-Amino-5-benzyl-4-(morpholino)pyrimidine
2-Amino-5-benzyl-4-(dimethylamino)pyrimidine
2-Amino-5-(4-methoxybenzyl)-4-(morpholino)pyrimidine
5-Benzyl-4-[2-(2-hydroxyethoxy)ethylamino]pyrimidine
2-Amino-5-benzyl-4-(4-hydroxypiperidino)pyrimidine
2-Amino-5-benzyl-4-(4-methylpiperazinoamino)pyrimidine
2-Amino-5-benzyl-4-(4-carbamoylpiperidino)pyrimidine
2-Amino-5-benzyl-4-(4-methylpiperazino)pyrimidine
2-Amino-5-benzyl-4-(4-hydroxyethylpiperazino)pyrimidine
5-Benzyl-2,4-bis(4-methylpiperazino)pyrimidine
5-Benzyl-2,4-(dimorpholino)pyrimidine
5-Benzyl-2-dimethylamino-4-(4-methylpiperazino)pyrimidine
2-Amino-5-(4-methylbenzyl)-4-(4-methylpiperazino)pyrimidine
2-Amino-4-(4-ethylpiperazino)-5-(4-methylbenzyl)pyrimidine
2-Amino-4-(4-hydroxyethylpiperazino)-5-(4-methylbenzyl)pyrimidine
2-Amino4-(4-hydroxypiperidino)-5-(4-methylbenzyl)pyrimidine
2-Amino-5-(4-chlorobenzyl)-4-(morpholino)pyrimidine
2-Amino-4-[2-(2-hydroxyethyl)ethylamino]-5-(4-chlorobenzyl)pyrimidine
2-Amino-5-(4-chlorobenzyl)-4-(4-methylpiperazino)pyrimidine
2-Amino-5-(4-chlorobenzyl)-4-(4-ethylpiperazino)pyrimidine
2-Amino-5-(4-chlorobenzyl)-4-(4-hydroxyethylpiperazino)pyrimidine
2-Amino-5-(4-chlorobenzyl)-4-(4-hydroxypiperidino)pyrimidine
2-Amino-5-(4-methoxybenzyl)-4-(4-methylpiperazino)pyrimidine
2-Amino-5-(4-hydroxybenzyl)-4-(4-methylpiperazino)pyrimidine
2-Amino-4-(4-methylpiperazino)-5-(4-isopropylbenzyl)pyrimidine
2-Amino-4-(4-ethylpiperazino)-5-(4-isopropylbenzyl)pyrimidine
2-Amino-4-(4-hydroxyethylpiperazino)-5-(4-isopropylbenzyl)pyrimidine
2-Amino-5-(4-hydroxypiperidino)-5-(4-isopropylbenzyl)pyrimidine
2-Amino-4-(4-methylpiperazino)-5-(3,4,5-trimethoxybenzyl)pyrimidine
2-Amino-4-(4-ethylpiperazino)-5-(3,4,5-trimethoxybenzyl)pyrimidine
2-Amino-4-(4-hydroxyethylpiperazino)-5-(3,4,5-trimethoxybenzyl)pyrimidine
2-Amino-4-(4-hydroxypiperidino)-5-(3,4,5-trimethoxybenzyl)pyrimidine
2-Amino-4-(4-methylpiperazino)-5-(4-[4-chlorobenzyloxy]benzyl)pyrimidine
2-Amino-4-(4-ethylpiperazino)-5-(4-[4-chlorobenzyloxy]benzyl)pyrimidine
2-Amino-4-(4-hydroxyethylpiperazino)-5-(4-[4-chlorobenzyloxy]benzyl)pyrimidine
2-Amino-4-(4-methylpiperazino)-5-((3-pyridyl)methyl)pyrimidine
2-Amino-4-(4-ethylpiperazino)-5-[(3-pyridyl)methyl]pyrimidine 2-Amino-4-(4-hydroxyethylpiperazino)-5-([3-pyridyl]methyl)pyrimidine
4-Anilino-2-methyl-5-(phenethyl)pyrimidine
4-Benzylamino-2-methyl-5-(phenethyl)pyrimidine
4-[2-(2-hydroxyethoxy)ethylamino]-2-methyl-5-(phenethyl)pyrimidine
2-Methyl-4-morpholino-5-(phenethyl)pyrimidine
2,4-Dimorpholino-5-(phenethyl)pyrimidine
2-Amino-4-morpholino-5-(phenethyl)pyrimidine
4-Morpholino-5-(phenethyl)pyrimidine
2-Amino-5-(4-methoxyphenethyl)-4-(morpholino)pyrimidine
2-Amino-4-morpholino-5-(phenylpropyl)pyrimidine
2-Amino-4-morpholino-5-(phenyl)pyrimidine
2-Amino-5-(4-fluorophenyl)-4-(morpholino)pyrimidine
2-Amino-5-(4-chlorophenyl)-4-(morpholino)pyrimidine
2-Amino-5-(4-bromophenyl)-4-(morpholino)pyrimidine
2-Amino-5-(4-ethylphenoxy)-4-(4-methylpiperazino)pyrimidine
2-Amino-5-(2,4-dichlorophenoxy)-4-(4-methylpiperazino)pyrimidine
2-Amino-5-(4-chloro-2-methylphenoxy)-4-(4-methylpiperazino)pyrimidine
2-Amino-5-(3-chlorophenoxy)-4-(4-(2-hydroxyethyl)piperazino)pyrimidine
2-Amino-5-(2-chlorophenoxy)-4-(4-(2-hydroxyethyl)piperazino)pyrimidine
2-Amino-5-(4-bromophenoxy)-4-(4-(2-hydroxyethyl)piperazino)pyrimidine
2-Amino-5-(4-fluorophenoxy)-4-(4-(2-hydroxyethyl)piperazino)pyrimidine
2-Amino-5-(3-fluorophenoxy)-4-(4-(2-hydroxyethyl)piperazino)pyrimidine
2-Amino-4-(4-(2-hydroxyethyl)piperazino)-5-(4-trifluoromethylphenoxy)pyrimidine
2-Amino-4-(4-(2-hydroxyethyl)piperazino)-5-(4-methylphenoxy)pyrimidine
2-Amino-4-(4-(2-hydroxyethyl)piperazino)-5-(3-methylphenoxy)pyrimidine
2-Amino-4-(4-(2-hydroxyethyl)piperazino)-5-(2-methylphenoxy))pyrimidine
2-Amino-5-(4-ethylphenoxy)-4-(4-(2-hydroxyethyl)piperazino)pyrimidine
2-Amino-4-(4-(2-hydroxyethyl)piperazino)-5-(4-isopropylphenoxy)pyrimidine
2-Amino-5-(4-butylphenoxy)-4-(4-(2-hydroxyethyl)piperazino)pyrimidine
2-Amino-4-(4-(2-hydroxyethyl)piperazino)-5-(4-methoxyphenoxy)pyrimidine
2-Amino-4-(4-(2-hydroxyethyl)piperazino)-5-(3-methoxyphenoxy)pyrimidine
2-Amino-4-(4-(2-hydroxyethyl)piperazino)-5-(2-methoxyphenoxy)pyrimidine
2-Amino-4-(4-(2-hydroxyethyl)piperazino)-5-(4-(trifluoromethoxy)phenoxy)pyrimidine
2-Amino-5-(2,4-dichlorophenoxy)-4-(4-(2-hydroxyethyl)piperazino)pyrimidine
2-Amino-5-(2,3-difluorophenoxy)-4-(4-(2-hydroxyethyl)piperazino)pyrimidine
2-Amino-5-(2,4-difluorophenoxy)-4-(4-(2-hydroxyethyl)piperazino)pyrimidine
2-Amino-5-(2,6-difluorophenoxy)-4-(4-(2-hydroxyethyl)piperazino)pyrimidine
2-Amino-5-(3,5-difluorophenoxy)-4-(4-(2-hydroxyethyl)piperazino)pyrimidine
2-Amino-5-(4-chloro-2-fluorophenoxy)-4-(4-(2-hydroxyethyl)piperazino)pyrimidine
2-Amino-5-(2-chloro-4-fluorophenoxy)-4-(4-(2-hydroxyethyl)piperazino)pyrimidine
2-Amino-5-(4-chloro-2-methylphenoxy)-4-(4-(2-hydroxyethyl)piperazino)pyrimidine
2-Amino-5-(4-chlorophenoxy)-4-(4-(2-pivaloyloxyethyl)piperazino)pyrimidine
2-Amino-4-(4-butyrylpiperazino)-5-(4-chlorophenoxy)pyrimidine
2-Amino-5-(4-chlorophenoxy)-4-(4-phenoxyacetylpiperazino)pyrimidine
2-Amino-4-(4-benzoylpiperazino)-5-(4-chlorophenoxy)pyrimidine
2-Amino-5-(4-chlorophenoxy)-4-(4-(2-furoyl)piperazino)pyrimidine
2-Amino-5-(4-chlorophenoxy)-4-(4-ethoxycarbonylpiperazino)pyrimidine
2-Amino-5-(4-chlorophenoxy)-4-(4-phenoxycarbonylpiperazino)pyrimidine
2-Amino-5-(4-chlorophenoxy)-4-(4-methoxydicarbonylpiperazino)pyrimidine
2-Amino-4-(4-(3-carbamoylpropionyl)piperazino)-5-(4-chlorophenoxy)pyrimidine
2-Amino-4-(4-(3-carboxypropionyl)piperazino)-5-(4-chlorophenoxy)pyrimidine
2-Amino-5-(4-chlorophenoxy)-4-(4-(methylsulfonyl)piperazino)pyrimidine
2-Amino-5-(4-chlorophenoxy)-4-(4-(phenylsulfonyl)piperazino)pyrimidine
5-(4-Chlorophenoxy)-4-(4-methylpiperazino)-2-(1-pyrrolidinyl)pyrimidine
2-(Anilino)-5-(4-chlorophenoxy)-4-(4-methylpiperazino)pyrimidine
5-(4-Chlorophenoxy)-2-(4-fluoroanilino)-4-(4-methylpiperazino)pyrimidine
2-(Benzylamine)-5-(4-chlorophenoxy)-4-(4-methylpiperazino) pyrimidine
2,4-Bis(4-ethylpiperazino)-5-(4-chlorophenoxy)pyrimidine
5-(4-Chlorophenoxy)-4-(4-(2-hydroxyethyl)piperazino)-2-(isopropylamino)pyrimidine
5-(4-Chlorophenoxy)-2-((2-hydroxyethyl)amino)-4-(4-(2-hydroxyethyl)piperazino)pyrimidine
5-(4-Chlorophenoxy)-2-(2-(2-hydroxyethoxy)ethylamino)-4-(4-(2-hydroxyethyl)piperazino)pyrimidine
2-(Anilino)-5-(4-chlorophenoxy)-4-(4-(2-hydroxyethyl)piperazino)pyrimidine
5-(4-Chlorophenoxy)-2-(4-fluoroanilino)-4-(4-(2-hydroxyethyl)piperazino)pyrimidine
5-(4-Chlorophenoxy)-4-(4-(2-hydroxyethyl)piperazino)-2-(4-methylanilino)pyrimidine
5-(4-Chlorophenoxy)-4-(4-(2-hydroxyethyl)piperazino)-2-(1-pyrrolidinyl)pyrimidine
5-(4-Chlorophenoxy)-4-(4-(2-hydroxyethyl)piperazino)-2-(piperidino)pyrimidine
5-(4-Chlorophenoxy)-4-(4-(2-hydroxyethyl)piperazino)-2-(4-hydroxypiperidino)pyrimidine
5-(4-Chlorophenoxy)-4-(4-(2-hydroxyethyl)piperazino)-2-(4-phenylpiperazino)pyrimidine
5-(4-Chlorophenoxy)-4-(4-(2-hydroxyethyl)piperazino)-2-(4-methylpiperazino)pyrimidine
5-(4-Chlorophenoxy)-2-(4-ethylpiperazino)-4-(4-(2-hydroxyethyl)piperazino)pyrimidine
2,4-Bis(4-(2-hydroxyethyl)piperazino)-5-(4-chlorophenoxy)pyrimidine
2-Chloro-5-(4-chlorophenoxy)-4-(4-(2-hydroxyethyl)piperazino)pyrimidine
5-(4-Chlorophenoxy)-4-(4-(2-hydroxyethyl)piperazino)pyrimidine 5-(4-Chlorophenoxy)-4-(4-methylpiperazino)pyrimidine
2-Amino-5-(4-chlorophenyl)-4-(4-(2-hydroxyethyl) piperazino)pyrimidine
2-Amino-5-(4-chlorophenyl)-4-(4-methylpiperazino) pyrimidine
2-Amino-5-(4-fluorobenzyl)-4-(4-methylpiperazino) pyrimidine
2-Amino-4-(4-hydroxyethylpiperazino)-5-(4-trifluoromethylbenzyl)pyrimidine
2-(4-Carbamoylpiperidino)-5-(4-methylbenzyl)-4-(4-methylpiperazino)pyrimidine
2-(2-Hydroxyethoxy)ethylamino)-5-(4-methylbenzyl)-4-(4-methylpiperazino)pyrimidine
2-Amino-5-(4-chlorophenethyl)-4-(4-methylpiperazino) pyrimidine
2-Amino-5-(4-chlorophenethyl)-4-(4-(2-hydroxyethyl) piperazino)pyrimidine
2-Amino-5-(4-chlorobenzyloxy)-4-(4-methylpiperazino) pyrimidine
2-Amino-5-(4-chlorobenzyloxy)-4-(4-(2-hydroxyethyl) piperazino)pyrimidine
2-Amino-5-(4-chlorophenoxy)-4-(4-hydroxypiperidino) pyrimidine
2-Amino-4-(4-hydroxypiperidino)-5-(4-methylphenoxy) pyrimidine
2-Amino-5-(2,4-dichlorophenoxy)-4-(4-hydroxypiperidino) pyrimidine
5-(4-Chlorophenoxy)-4-(4-hydroxypiperidino)-2-morpholinopyrimidine
2-Amino-5-(4-chlorophenoxy)-4-(3-(hydroxymethyl) piperidino)pyrimidine
2-Amino-5-(4-chlorophenoxy)-4-(2-(2-hydroxyethyl) piperidino)pyrimidine
5-(4-Chlorophenoxy)-4-(2-(2-hydroxyethoxy)ethylamino)-2-morpholinopyrimidine
2-Anilino-4-(4-hydroxypiperidino)-5-(4-methylbenzyl) pyrimidine
2,4-Bis-(4-Hydroxypiperidino)-5-(4-methylbenzyl) pyrimidine
4-(4-Hydroxypiperidino)-5-(phenethyl)pyrimidine
2-Amino-4-(4-carbamoylpiperidino)-5-(4-chlorophenethyl) pyrimidine
and pharmaceutically acceptable salts or solvates thereof.

In one aspect of the invention there is provided the compounds according to the invention for use in medical therapy particularly for the treatment of neurodegenerative or neurological disorders of the central or peripheral nervous systems.

Examples of nervous system disorders which may be treated in accordance with the invention include dementing disorders such as age-related senility, senile dementia or Age Related Mental Impairment (ARMI), cerebal ataxia, Parkinson's disease, Alzheimer's disease, peripheral neuropathy, cognitive disorders secondary to stroke or trauma and attention-deficit hyperactivity disorder.

In a further aspect of the present invention there is included:

a) A method for the treatment of neurodegenerative or neurological disorders of the central or peripheral nervous systems which comprises treating the subject e.g., a mammal, such as a human, with a therapeutically effective amount of a compound according to the invention.

b) Use of a compound according to the invention in the manufacture of a medicament for the treatment of any of the above-mentioned disorders.

Examples of pharmaceutically acceptable salts of the compounds according to the invention include acid addition salts. However, salts of non-pharmaceutically acceptable acids may be of utility in the preparation and purification of the compound in question.

Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethansulfonic, p-toluenesulfonic, benzenesulfonic and isethionic acids.

The compounds according to the invention and pharmaceutically acceptable salts or solvates thereof may be employed in combination with other therapeutic agents for the treatment of the above disorders. Examples of such further therapeutic agents include Cognex®, Aricept® and other agents (e.g., acetylcholine esterase inhibitors, muscarinic or nicotinic receptor agonists, MAO inhibitors) that are effective for the treatment of neurodegenerative or neurological disorders of the central or peripheral nervous systems. The component compounds of such combination therapy may be administered simultaneously in either separate or combined formulations, or at different times, e.g., sequentially such that a combined effect is achieved.

While it is possible for compounds according to the invention to be administered as the raw chemical, it is preferable to present them as a pharmaceutical formulation. The formulations of the present invention comprise a compound of Formula I, as above defined, or a pharmaceutically acceptable salt thereof, together with one or more pharmaceutically acceptable carriers therefor and optionally other therapeutic ingredients. The carrier(s) must be acceptable in the sense of being compatible with the other ingredients of the formulation and not deleterious to the recipient thereof.

The formulations include those suitable for oral, parenteral (including subcutaneous, transdermal, intradermal, intramuscular and intravenous), rectal and topical (including dermal, buccal and sublingual) administration although the most suitable route may depend upon, for example, the condition and disorder of the recipient. The formulations may conveniently be presented in unit dosage form and may be prepared by any of the methods well know in the art of pharmacy. All methods include the step of bringing into association a compound of Formula I or a pharmaceutically acceptable salt thereof (active ingredient) with the carrier which constitutes one or more accessory ingredients. In general the formulations are prepared by uniformly and intimately bringing into association the active ingredients with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a nonaqueous liquid; or as an oil-in-water liquid emulsion, or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacterioistats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophillised) condition requiring only the addition of the sterile liquid carrier, for example, water-for-injection, immediately prior to use. Extemporaneous injection solutions and suspensions may be prepared from sterile powders, granules and tablets of the kind previously described.

Formulations suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 35%, preferably about 3% to 15%. As one particular possibility, the active compound may be delivered from the patch by electrotransport or iontophoresis, as generally described in Pharmaceutical. Res., 3(6), 318 (1986).

Formulations for rectal administration may be presented as suppository with the usual carriers such as cocoa butter or polyethylene glycol.

Formulations for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

Tablets or other forms of presentation in discrete units may conveniently contain an amount of compound of the Formula I which is effective for each of the above-mentioned indications at such dosage or as a multiple of the same, for instance, units containing 5 mg to 500 mg, usually between 10 mg to 250 mg.

For the above-mentioned conditions and disorders, the compounds of the Formula I are preferably administered orally or by injection (intraparenteral or subcutaneous). The precise amount of compound administered to a patient will be the responsibility of the attendant physician. However, the dose employed will depend on a number of factors, including the age and sex of the patient, the precise disorder being treated, and its severity. Also the route of administration is likely to vary depending on the condition and its severity.

For each of the above-mentioned indications the compounds of the Formula I may be administered orally. The dose range for adult humans is generally from about 10 to 4000 mg/day and preferably from about 100 to 1000 mg/day. It may be advantageous to administer an initial dose of 200 to 2000 mg the first day then a lower dose of 100 to 1000 mg on subsequent days.

For each of the above-mentioned indications, the compounds according to the invention may be administered by injection at a dose of from 30 to 800 mg/kg per day.

The present invention further includes processes for the preparation of compounds of Formula I and salts or solvates thereof.

The compounds of formula (I) and their esters, amides, salts and solvates may be prepared in any manner known in the art for the preparation of compounds of analogous structure, for example, in accordance with the present invention, by those methods hereinafter described.

The compounds, esters, amides, salts and solvates of formula (I) wherein R1 is attached to the 4-position of the pyrimidine ring and W—X is attached at the 5-position of the pyrimidine ring may thus be prepared by a process which comprises:

reacting a compound of formula (IIA)

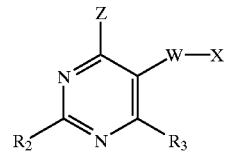

Formula IIA wherein R2, R3, W and X are as hereinbefore defined and Z is a leaving group, with an amine NR'R" (wherein R' and R" are as defined for $R^1$) or a suitable derivative thereof. Suitable leaving groups include halogens such as chlorine. The reaction is carried out in an organic solvent (e.g., ethanol, N,N-dimethylformamide) at a temperature of approximately 20° C. to approximately 100° C. The compound of formula (IIA) may be isolated and purified prior to reaction with an amine NR'R" or may be used in situ.

Compounds of formula (IIA), wherein $R^2$, $R^3$, W and X are as hereinbefore defined and Z is a 1-(4-formylpiperazino), 1-(4-substituted cabonylpiperazino) or 1-(4-substituted sulfonylpiperazino) derivative, can be prepared from compounds of formula (IIA), wherein $R^2$, $R^3$, W and X are as hereinbefore defined and Z is 1-(piperazino), by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C.

Compounds of formula (IIA) wherein Z is a halogen atom can be prepared from compounds of formula (IIA)

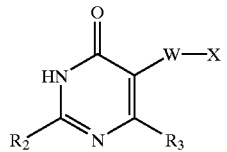

Formula IIIA wherein $R^2$, $R^3$, W and X are as hereinbefore defined by reaction with a halogenating agent (e.g., Vilsmeier reagent (e.g., oxalyl chloride and N,N-dimethylformamide, oxalyl chloride and 1-formylmorpholine, oxalyl chloride and N,N-diisopropylformamide), phosphorous oxychloride, phosphorous pentachloride, thionyl chloride) in a suitable organic solvent (e.g., dichloromethane, 1,2-dichlorethane, toluene, N,N-dimethlyformamide) at a temperature of approximately 40° C. to approximately 100° C.

Compounds of formula (IIIA) can be prepared from compounds of formula (IVA)

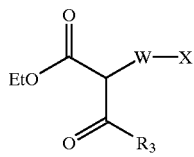

Formula IVA wherein $R^3$, W and X are as hereinbefore defined by reaction of an alkaline earth salt of (IVA) with formamidine or a derivative of formamidine (e.g., guanidine, N,N-dialkylguanidine, N-phenylguanidine, thiourea, 2-ethyl-2-thiopseudourea, acetamidine) in a suitable organic solvent (e.g., ethanol, methanol, 2-propanol, tert-butanol, tetrahydrofuran) at a temperature of approximately 60° C. to the reflux temperature.

Compounds of formula (IVA) can be prepared from compounds of formula (VA)

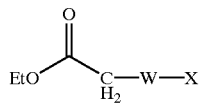

Formula VA where in W and X are as hereinbefore defined by reaction with an ester (e.g., ethyl formate, ethyl acetate, ethyl benzoate, ethyl trifluoroacetate) and a strong base (e.g., sodium hydride, potassium hydride, potassium tert-butoxide, sodium metal, lithium diisopropylamine) in a suitable organic solvent (e.g., tetrahydrofuran, ether, toluene) at a temperature of approximately 0° C. to approximately 40° C.

Compounds of formula (VA) can be prepared by various methods known in the art or are available from commercial sources.

The compounds, esters, amides, salts and solvates of formula (!) wherein R1 is attached to the 5-position of the pyrimidine ring and W—X is attached to the 4-position of the pyrimidine ring may thus be prepared by a process which comprises:
reacting a compound of formula (IIB)

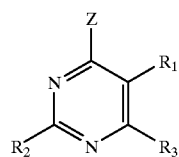

Formula IIB wherein $R^1$, $R^2$ and $R^3$ are as hereinbefore defined and Z is a leaving group, with an amine NHCH2X or NHRX (wherein R and X are as defined hereinbefore) or an alcohol HOX or HOCH2X or a suitable derivative thereof. Suitable leaving groups include halogens such as chlorine. The reaction is carried out with a suitable base (e.g., 4-dimethylaminopyridine, pyridine, triethylamine, potassium carbonate, sodium hydride, potassium t-butoxide) in a suitable organic solvent (e.g., tetrahydrofuran, acetone, methanol, pyridine, N,N-dimethylformamide) at a temperature of approximately 20° C. to approximately 100° C. The compound of formula (IIA) may be isolated and purified prior to reaction with an amine NR'R" or may be used in situ.

Compounds of formula (IIB) wherein Z is a halogen atom can be prepared from compounds of formula (IIIB)

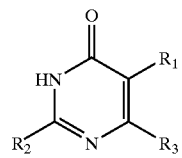

Formula IIIB wherein $R^1$, $R^2$ and $R^3$ are as hereinbefore defined by reaction with a halogenating agent (e.g., Vilsmeier reagent (e.g., oxalyl chloride and N,N-dimethylformamide, oxalyl chloride and 1-formylmorpholine, oxalyl chloride and N,N-diisopropylformamide), phosphorous oxychloride, phosphorous pentachloride, thionyl chloride) in a suitable organic solvent (e.g., dichloromethane, 1,2-dichlorethane, toluene, N,N-dimethylformamide) at a temperature of approximately 40° C. to approximately 100° C.

Compounds of formula (IIIB) can be prepared from compounds of formula (IVB)

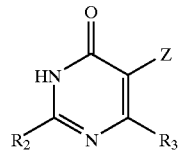

Formula IVB wherein $R^2$ and $R^3$ are as hereinbefore defined and Z is a leaving group, with an amine NR'R" (wherein R' and R" are as defined for $R^1$) or a suitable derivative thereof. Suitable leaving groups include halogens such as bromine. The reaction is carried out in an organic solvent (e.g., dioxane, ethanol, N,N-dimethylformamide) or in neat amine at a temperature of approximately 20° C. to approximately 100° C.

Compounds of formula (IVB) can be prepared from compounds of formula (VB)

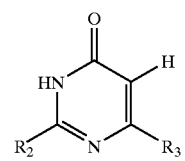

Formula VB wherein $R^2$ and $R^3$ are as hereinbefore defined by reaction with a halogenating reagent (e.g., bromine, N-bromosuccinimide, iodine monobromide, iodine monochloride or iodine) and optionally with a base (e.g., sodium hydride) in a suitable solvent (e.g., tetrahydrofuran, acetic acid, water) at a temperature of approximately 0° C. to approximately 400 ° C.

Compounds of formula (VB) can be prepared by various methods known in the art or are available from commercial sources.

Specifically preferred intermediate compounds for synthesis of the above-listed specifically preferred compounds of Formula I are:
5-(Phenoxy)isocytosine
5-(4-Methylphenoxy)isocytosine
5-(4-Fluorophenoxy)isocytosine
b 5-(4-Chlorophenoxy)isocytosine
5-(4-Chlorophenoxy)uracil
2-Methoxy-5-(phenoxy)pyrimidin4(3H)-one
5-(4-Chlorophenoxy)-2-(mercapto)pyrimidin-4(3H)-one
5-(4-Chlorophenoxy)-2-(methylthio)pyrimidin-4(3H)-one
5-(4-chlorophenoxy)-2-(4-methylpiperazino)pyrimidin-4(3H)-one
5-(4-chlorophenoxy)-2-(4-methylpiperazino)pyrimidin-4(3H)-one
5-(4-Chlorophenoxy)-2-(dimethylamino)pyrimidin-4(3H)-one
5-Benzyl-2,4-dichloropyrimidine
5-(3,4,5-Trimethoxybenzyl)isocytosine
5-Benzyl-2-(methylthio)pyrimidin-4(3H)-one
5-(4-Chlorobenzyl)isocytosine
5-(4-Isopropylbenzyl)isocytosine
5-(4-Methoxybenzyl)isocytosine
2-Methyl-5-(phenethyl)pyrimidin-4(3H)-one
5-(Phenethyl)isocytosine
5-(4-Methoxyphenethyl)isocytosine
5-(Phenylpropyl)isocytosine
2-Methyl-5-(phenylpropyl)pyrimidin-4(3H)-one
5-(4-Bromophenyi)isocytosine
5-(4-Fluorophenyl)isocytosine
5-(4-Chlorophenyl)isocytosine
2-Chloro-4-morpholino-5-(phenethyl)pyrimidine
5-Benzyl-2-chloro-4-(4-methylpiperazino)pyrimidine
5-Benzyl-2-chloro-4-(morpholino)pyrimidine
5-Benzyl-2-chloro-4-[2-(2-hydroxyethoxy)ethyl]pyrimidine
5-Benzyl-2-chloro-4-(4-hydroxypiperidino)pyrimidine
5-[4-(4-Chlorobenzyloxy)benzyl]isocytosine
5-(4-Methylbenzyl)isocytosine
5-[(3-Pyridyl)methyl]isocytosine
4-Chloro-2-morpholino-5-(phenethyl)pyrimidine
5-(Morpholino)isocytosine
5-(4-Methylpiperazino)isocytosine
5-(4-Methylpiperazino)pyrimidin-4(3H)-one
5-(4-Chlorophenethyl)isocytosine
5-(4-Chlorophenoxy)-2-morpholinopyrimidin4(3H)-one
5-(4-Chloro-2-methylphenoxy)isocytosine
5-(4-Chlorophenoxy)pyrimidin-4(3H)-one
5-(4-Chlorophenoxy)-2,4-dichloropyrimidine
2-Chloro-5-(4-chlorophenoxy)-4-(4-methylpiperazino)pyrimidine
5-(4-Methylbenzyl)uracil
5-(4-Ethylphenoxy)isocytosine
5-(3-Chlorophenoxy)isocytosine
5-(3-Fluorophenoxy)isocytosine
5-(4-Chloro-2-fluorophenoxy)isocytosine
5-(2,4-Dichlorophenoxy)isocytosine
5-(2,3-Difluorophenoxy)isocytosine
5-(4-Trifluoromethoxyphenoxy)isocytosine
5-(2-Methylphenoxy)isocytosine
5-(3-Methylphenoxy)isocytosine
5-(4-Chlorophenoxy)-2-(4-fluoroanilino)pyrimidin-4(3H)-one
5-(4-Bromophenoxy)isocytosine
5-(2-Chlorophenoxy)isocytosine
5-(2-Methyloxyphenoxy)isocytosine
5-(3-Methyloxyphenoxy)isocytosine
5-(4-Methyloxyphenoxy)isocytosine
5-(4-Isopropylphenoxy)isocytosine
5-(4-Trifluoromethylphenoxy)isocytosine
5-(2,4-Difluorophenoxy)isocytosine
5-(3,4-Difluorophenoxy)isocytosine
5-(4-Chlorophenoxy)-2-(diisopropylaminomethyleneamino)pyrimidin4(3H)-one
5-(4-Chlorophenoxy)-2-(diisopropylaminomethyleneamino)4-(4-(2-hydroxyethyl)piperazino)pyrimidine
5-(4-Chlorophenoxy)-2-(diisopropylaminomethyleneamino)-4-(2-(2-hydroxyethoxy)ethylamino)pyrimidine Esters and amides of compounds of Formula I can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C.

Salts of the compounds of Formula I can be made from the free base form by reaction with the appropriate acid.

The following Examples illustrate the present invention but should not be construed as a limitations to the scope thereof.

EXAMPLES

Example 1

Preparation of intermediate compound 5-(4-chlorophenoxy)isacytosine a) Preparation of ethyl 4chlorophenoxyacetate A solution of 4-chlorophenoxyacetate acid (Aldrich) (18.62 g, 99.8 mmoles) and concentrated sulfuric acid (Fisher) (2.5 mL) in ethanol (170 mL) was refluxed with stirring under a Drierite tube for 96 hours. The reaction solution was cooled in an ice-bath, and the volatiles were removed by spin evaporation in vacuo to a volume of about 100 mL. The liquid was dissolved in dichloromethane (225 mL) and washed with a solution of 5% aqueous sodium bicarbonate (4×100 mL) and finally with brine (1×50 mL). The solution was dried over sodium sulfate and spin evaporated in vacuo to give 19.97 g (93% yield) of ethyl 4-chlorophenoxyacetate as an amber liquid.

b) Preparation of 5-(4chlorophenoxy)isocytosine

A solution of ethyl 4chlorophenoxyacetate (19.90 g, 92.7 mmoles) and ethyl formate (Acros) (30 mL, 371 mmoles) in tetrahydrofuran (100 mL) was added dropwise to a stirred dispersion of sodium hydride (60% dispersion in mineral oil) (Aldrich) (5.31 g, 132.7 mmoles) in tetrahydrofuran (50 mL). After 30 minutes, when about 60% of the solution had been added, the reaction was cooled with an ice-bath to slow the reaction. After a total of 1 hour addition was complete, the addition funnel was rinsed with tetrahydrofuran (15 mL), and the reaction mixture was stirred at ambient temperature for 16 hours. The solution was cooled on an ice-bath and ethanol (11 mL) was added. The volatiles were removed by spin evaporation in vacuo to give the sodium salt of ethyl 2-formyl-2-(4-chlorophenoxy)acetate as a syrup that solidified after several hours. The solid was largely dissolved in ethanol (100 mL) and combined with a white mixture prepared from mixing sodium methoxide (Aldrich) (6.04 g, 106.2 mmoles) and guanidine carbonate (Aldrich) (10.05 g, 55.7 mmoles) in ethanol (75 mL). The reaction mixture was refluxed with stirring for 6 hours. The reaction mixture was cooled on an ice-bath, and the volatiles were removed by spin evaporation in vacuo to give a semi-solid residue, which was dissolved in cold water to a volume of 500 mL. The solution was vigorously stirred and carefully acidified to pH 5 with acetic acid (15 mL), which was added in 3 equal portions. The cream colored mixture was stirred for 2 hours. The solid was collected, washed extensively with water (750 mL), and vacuum suction air dried to give the crude solid. The solid was heated with stirring in ethanol to a final volume of 200 mL. The cooled mixture was collected, washed with ethanol and dried to give 16.83 g (76% yield) of 5-(4-chlorophenoxy)isocytosine as a white solid, mp 245° C.

Example 2

Preparation of 2-amino-5-(4-chlorophenoxy)-4-(piperazino)pyrimidine

A solution of oxalyl chloride (Acros) (8.936 g, 70.4 mmoles) in dichloromethane (5 mL) was added in ten equal portions to a stirred, ice-bath cooled solution of diisopropylformamide (Aldrich) (10.057 g, 77.8 mmoles) in dichloromethane (300 mL). The ice-bath was removed, and the clear solution was stirred at ambient temperature for 40 minutes. Solid 5-(4-chlorophenoxy)isocytosine (6.022 9, 25.33 mmoles) was added, and the mixture was refluxed with stirring for 1 hour. The resultant solution was cooled and poured into an ice-bath cooled solution of vigorously stirred saturated aqueous sodium bicarbonate (400 mL). The layers were separated, and the organic phase was washed with ice cold water (200 mL), ice cold brine (100 mL) and then dried over sodium sulfate. The dry solution was spin evaporated in vacuo to give the intermediate chloropyrimidine as an unstable yellow solid. The yellow solid was dissolved in ethanol (80 mL), and added to a solution of anhydrous piperazine (Acros) (40.29 g, 467.7 mmoles) in ethanol (110 mL). The reaction was refluxed with stirring for 20 hours. Sodium hydroxide pellets (Aldrich) (19.624 g, 490.6 mmoles) and water (75 mL) was added to the cooled solution, and the reaction was refluxed with stirring for 20 hours. The volatiles were removed by spin evaporation in vacuo to a volume of about 250 mL. This solution was diluted with portions of ice and cold water with vigorous stirring to a volume of 1 L. The solid material was collected, washed with ice water (2×100 mL), air dried by vacuum suction and dried at 75° C. in vacuo to give 5.919 g (76% yield) of 2-amino-5-(4-chlorophenoxy)-4-(piperazino) pyrimidine as a white solid, mp 93–95° C.

Example 3

Preparation of 2-amino-5-(4-chlorophenoxy)-4-(4-formylpiperazino)pyrimidine

Ethyl formate (Acros) (11 mL) was added to a solution of 2-amino-5-(4-chlorophenoxy)-4-(piperazino)pyrimidine (0.433 g, 1.41 mmoles) in methanol, and after 16 hours the solution was spin evaporated in vacuo to give a colorless syrup. The syrup was triturated under hexanes containing 1% ethyl acetate to give a solid that was collected and recrystallized from ethyl acetate to give 0.250 g (53% yield) of 2-amino-5-(4-chlorophenoxy)-4-(4-formylpiperazino) pyrimidine as white crystals, mp 159–161° C.

Example 4

Preparation of 2-amino-5-(4-chlorophenoxy)-4-(4-(2-hydroxyethyl)piperazino)pyrimidine A solution of oxalyl chloride (Acros) (2.267 g, 17.86 mmoles) in dichloromethane (5 mL) was added in several portions to a stirred, ice-bath cooled solution of diisopropylformamide (Aldrich) (2.522 g, 19.52 mmoles) in dichloromethane (65 mL). The ice-bath was removed, and the clear solution was stirred at ambient temperature for 50 minutes. Solid 5(4-chlorophenoxy)isocytosine (1.030 g, 4.33 mmoles) was added with dichloromethane (20 mL), and the mixture was refluxed with stirring for 0.5 hour. The resultant solution was cooled and poured into an ice-bath cooled solution of vigorously stirred, saturated aqueous sodium bicarbonate (300 mL). The layers were separated, and the organic phase was washed with ice cold water (3×100 mL), ice cold brine (100 mL) and then dried over sodium sulfate. The dry solution was spin evaporated in vacuo to give the intermediate chloropyrimidine as a syrup. The syrup was dissolved in ethanol (100 mL), 1-(2-hydroxyethyl) piperazine (Aldrich) (5.07 g, 38.94 mmoles) and ethanol (40 mL) were added, and the reaction was refluxed with stirring for 45 hours. Sodium hydroxide pellets (Aldrich) (5.68 g, 142 mmoles) and water (150 mL) were added to the cooled solution, and the reaction was refluxed with stirring for 2 hours. The volatiles were removed by spin evaporation in vacuo to a small volume, and the residue was dissolved in dichloromethane containing 5% ethanol (250 mL). The solution was washed with water (6×100 mL) until the washings were neutral to pH paper, brine (100 mL) and then dried over sodium sulfate. The dry solution was spin evaporate in vacuo to give a white solid that was recrystallized from ethylacetate to give 0.449 g (29% yield) of 2-amino-5-(4-chlorophenoxy)-4-(4-(2-hydroxyethyl)piperazino) pyrimidine as a white powder, mp 121–123° C.

Example 5

Preparation of 2-amino-5-(4-chlorophenoxy)-4-(4-methylpiperazino)pyrimidine

A solution of oxalyl chloride (Acros) (1.111 g, 8.75 mmoles) in dichloromethane (5 mL) was added in several portions to a stirred, ice-bath cooled solution of diisopropylformamide (Aldrich) (1.306 g, 10.10 mmoles) in dichloromethane (75 mL). The ice-bath was removed, and the clear solution was stirred at ambient temperature for 30 minutes. Solid 5-(4-chlorophenoxy)-isocytosine (0.518 g, 2.18 mmoles) was added, and the mixture was refluxed with stirring for 0.5 hour. The resultant solution was cooled and poured into an ice-bath cooled solution of vigorously stirred, saturated aqueous sodium bicarbonate (200 mL). The layers were separated, and the aquous layer was extracted with dichloromethane (60 mL). The combined organic layers were washed with ice cold water (2×100 mL), ice cold brine (100 mL) and then dried over sodium sulfate. The dry solution was spin evaporated in vacuo to give the intermediate chloropyrimidine as a yellow liquid. The liquid was dissolved in ethanol (100 mL), 1-methylpiperazine (Aldrich) (3.723 g, 37.10 mmoles) was added, and the reaction was refluxed with stirring for 19 hours. Sodium hydroxide pellets (Aldrich) (3.30 g, 82.5 mmoles) and water (100 mL) was added to the cooled solution, and the reaction was refluxed with stirring for 4 hours. The volatiles were removed by spin evaporation in vacuo to a small volume, and the residue was dissolved in dichloromethane (200 mL). The solution was washed with water (5×100 mL) until the washings were neutral to pH paper, brine (100 mL) and then dried over sodium sulfate. The dry solution was spin evaporated in vacuo to give a clear liquid that was dissolved in ethyl acetate (5 mL). The resultant colorless crystals were collected and dried to give 0.107 g (15% yield) of 2-amino-5-(4-chlorophenoxy)-4-(4-methylpiperazino)pyrimidine as a white powder, mp 143–1440° C.

Example 6

Preparation of 2-amino-5-(4-chlorophenoxy)-4-(2-(2-hydroxyethoxy)ethylamino)pyrimidine hydrochloride A solution of oxalyl chloride (Acros) (0.961 g, 7.57 mmoles) in dichloromethane (5 mL) was added in several portions to a stirred, ice-bath cooled solution of diisopropylformamide (Aldrich) (1.177 g, 9.11 mmoles) in dichloromethane (35 mL). The ice-bath was removed, and the clear solution was stirred at ambient temperature for 50 minutes. Solid 5-(4-chlorophenoxy)-isocytosine (0.562 g, 2.36 mmoles) and dichloromethane (35 mL) was added, and the mixture was refluxed with stirring for 1 hour. The resultant solution was cooled and poured into an ice-bath cooled solution of vigorously stirred, saturated aqueous sodium bicarbonate (200 mL). The layers were separated, and the organic phase was washed with ice cold water (100 mL), ice cold brine (50 mL) and then dried over sodium sulfate. The dry solution was spin evaporated in vacuo to give the intermediate chloropyrimidine as a yellow liquid. The liquid was dissolved in ethanol (25 mL) and 2-(2-aminoethoxy)ethanol (Acros) (4.75 g, 45.18 mmoles) and ethanol (10 mL) were added. The reaction was refluxed with stirring for 21 hours. Sodium hydroxide pellets (Aldrich) (2.45 g, 61.25 mmoles) and water (25 mL) was added to the cooled solution, and the reaction was refluxed with stirring for 44 hours. The volatiles were removed by spin evaporate in vacuo to a small volume, and the residue was partioned between dichloromethane (100 mL) and water (40 mL). The layers were separated, and the dichloromethane solution was washed with water (6×40 mL) until the washings were neutral to pH paper, brine (80 mL) and then dried over sodium sulfate. The dry solution was spin evaporated in vacuo to a clear liquid. The liquid was dissolved in ethanol (50 mL), 37% hydrochloric acid (3 mL) was added, and the solution was spin evaporated in vacuo to give a light brown oil. The oil was triturated under ethyl ether to give a solid that was collected and recrystallized from acetone-ethanol to give 0.177 g (20% yield) of 2-amino-5-(4-chlorophenoxy)-4-(2-(2-hydroxyethoxy)ethylamino)pyrimidine hydrochloride as beige crystals, mp 140–141° C.

Example 7

Preparation of 2-amino4-(4-carbamoylpiperidino)-5-(4-chlorophenoxy)pyrimidine

A solution of oxalyl chloride (Acros) (1.103 g, 8.69 mmoles) in dichloromethane (5 mL) was added in several equal portions to a stirred, ice-bath cooled solution of diisopropylformamide (Aldrich) (1.345 g, 10.41 mmoles) in dichloromethane (95 mL). The ice-bath was removed, and the clear solution was stirred at ambient temperature for 45 minutes. Solid 5-(4-chlorophenoxy)isocytosine (1.04 g, 4.37 mmoles) was added, and the mixture was refluxed with stirring for 1.25 hours. The resultant solution was cooled and poured into an ice-bath cooled solution of vigorously stirred saturated aqueous sodium bicarbonate (350 mL). The layers were separated, and the organic phase was washed with ice cold water (100 mL), ice cold brine (75 mL) and then dried over sodium sulfate. The dry solution was spin evaporated in vacuo to give the intermediate chloropyrimidine as a yellow residue. This residue was dissolved in methanol (90 mL), combined with isonipecotamide (Aldrich) (4.150 g, 31.4 mmoles) in methanol (10 mL) and refluxed with stirring for 20 hours. Sodium hydroxide pellets (Aldrich) (1.093 g, 27.3 mmoles) and water (150 mL) were added to the cooled solution. The reaction was refluxed with stirring for 3 hours. The hot solution was filtered through flutted filter paper, seeded, and allowed to cool. The white clumps of crystals that formed were collected and washed with methanol-water: 1-1 (40 mL) and water. Recrystallization from ethyl acetate-ethanol gave 0.263 g (17%) of 2-amino4-(4-carbamoylpiperidine)-5-(4-chlorophenoxy)pyrimidine as colorless crystals, mp 208–211° C.

Example 8

Preparation of 2-amino-5-(4-chlorophenoxy)-4-(morpholino)pyrimidine

A solution of oxalyl chloride (Acros) (3.768 g, 29.68 mmoles) in dichloromethane (10 mL) was added in several equal portions to a stirred, ice-bath cooled solution of N-formylmorpholine (Acros) (3.944 g, 34.26 mmoles) in dichloromethane (100 mL). The ice-bath was removed, and the reaction was stirred at ambient temperature for 90 minutes. Solid 5-(4-chlorophenoxy)isocytosine (2.31 g, 9.72 mmoles) and dichloromethane (150 mL) was added, and the mixture was refluxed with stirring for 1.5 hour. The volatiles were removed by spin evaporated in vacuo to give a dark red oil, which was dissolved in methanol (100 mL) and combined with morpholine (Acros) (6.01 g, 68.98 mmoles). The reaction was refluxed with stirring for 3 hours. Sodium hydroxide pellets (Aldrich) (5.01 g, 125 mmoles) and water (60 mL) was added to the cooled solution, and the reaction was refluxed with stirring for 26 hours. The solution was diluted with water (60 mL), and the volatiles were removed by spin evaporate in vacuo to a volume of about 100 mL. The solid was collected, washed with water and air dried by vacuum suction to give a white solid. This material was recrystallized from methanol-water to give 1.433 g (48% yield) of 2-amino-5-(4-chlorophenoxy)-4-(morpholino)pyrimidine as white pins, mp 138–140° C.

Example 9

Preparation of 4-(4-acetylpiperazino)-2-amino-5-(4-chlorophenoxy)pyrimidine

Acetic anhydride (Aldrich) (0.318 g, 3.11 mmoles) in tetrahydrofuran (1.5 mL) was added to a solution of 2-amino-5-(4-chlorophenoxy)-4-(piperazino)pyrimidine (0.511 g, 1.67 mmoles) and triethylamine (0.526 g, 5.20 mmoles) in tetrahydrofuran (13 mL). After 0.5 hours the solution was diluted with ice water (40 mL) and poured into dichloromethane (75 mL). The layers were separated, and the organic layer was washed with saturated aqueous sodium bicarbonate (40 mL), brine (40 mL) and then dried over sodium sulfate. The dry solution was spin evaporated in vacuo to give a white foam. The foam was recrystallized from hexanes-ethyl acetate to give 0.348 g (60% yield) of 4-(4-acetylpiperazino)-2-amino-5-(4-chlorophenoxy)pyrimidine as beige pins, mp 153–157° C.

Example 10

Preparation of 5-(4-chlorophenoxy)-4-morpholino-2-(3-phenylureido)pyrimidine

Phenylisocyanate (0.24 g, 2.01 mmoles) in acetone (1 mL) was added to a stirred solution of 2-amino-5-(4-chlorophenoxy-4-(morpholino)pyrimidine (0.485 g, 1.58 mmoles) in tatrahydrofuran (11 mL), which was cooled on an ice-bath. After 16 hours the white crystals were collected, washed with a few mL of ethyl acetate and with hexanes, and dried to give 0.271 g (40% yield) of 5-(4-chlorophenoxy)-4-morpholino-2-(3-phenylureido) pyrimidine as a white solid, mp 229–231° C.

Example 11

Preparation of 2-amino-5-benzyl-4-(dimethylamino) pyrimidine

This compound was prepared in an analogous manner to that of Example 8 with replacement of diisopropylformamide with dimethylformamide (Aldrich). The reaction mixture was cooled to give crystalline product which was collected, washed with water and dried to give 2-amino-5-benzyl-4-(dimethylamino)pyrimidine as white crystals, mp 181–182° C.

Example 12

Preparation of 5-benzyl-4-[2-2-(2-hydroxyethoxy) ethylamino]pyrimidine

A mixture of 5-benzyl-2-chloro-4-[2-(2-hydroxyethoxy) ethylamino]pyrimidine (3.50 g, 12.08 mmoles), ethanol (190 mL) and 10% Pd on carbon (Aldrich) (0.84 g) was shaken in to presence of hydrogen at 2–3 atm for 17 hours. The reaction mixture was filtered through a pad of CELITE®, and the filtrates were spin evaporated in vacuo. The residual syrup was dissolved in dichloromethane (40 mL) and washed with water (20 mL) brine (20 mL) and then dried over sodium sulfate. The dry solution was spin evaporated in vacuo to give a residue that was triturated under hexanes to give 0.15 g (5% yield) of 5-benzyl-4-[2-(2-hydroxyethoxy)ethylamino]pyrimidine as a white solid, mp 86–87° C.

Example 13

Preparation of 5-(4-chlorophenoxy)-2-(methylmercapto)pyrimidine-4(3H)-one

Idomethane (Aldrich) (2.8 mL. 45 mmoles) was added to a solution of 5-(4-chlorophenoxy)-2-(mercapto)pyrimidine-4(3H)-one (10.24 g, 40 mmoles) in methanol (52 mL) and 1.0 N aqueous sodium hydride (40 mL). The resultant mixture was stirred at ambient temperature for 5.5 hours, then heated at 60° C. for 30 minutes. The mixture was spin evaporated in vacuo to give a solid, which was triturated with ice-water and then collected by suction filtration. Half of the light brown solid was recrystallized from ethyl acetate and half from ethanol to give 7.06 g (88% yield) of 5-(4-chlorophenoxy)-2(methylmercapto)pyrimidin-4-(3H)-one as a fluffy off-white solid, mp 232–233° C.

Example 14

Preparation of 5-(4-chlorophenoxy)-2-(4-methylpiperazino)pyrimidin-4(3H)-one

A solution of of 5-(4-chlorophenoxy)-2-(methylmercapto)pyrimidin-4(3H)-one (158 g, 5.87 mmoles) and 1-methylpiperazine (Aldrich) (6.1 mL, 55 mmoles) was heated at 135° C. for 18 hours. The dark brown mixture was spin evaporated in vacuo. The residue was dissolved in ethyl acetate and applied to a column (d=5 cm) of Silica Gel 80 that was equilibrated with ethyl acetate. The column was eluted with ethyl acetate by flash chromatography to remove unreacted starting material. Elution with 10% methanol-dichloromethane and spin evaporation in vacuo of the combined fractions gave a beige solid that was triturated with ethyl acetate to give 0.70 g (37% yield) of 5-(4-chlorophenoxy)-2-(4-methylpiperazino)pyrimidin-4(3H)-one. Recrystallization from ethyl acetate gave off-white flakes that had an NMR spectrum consistent with the assigned structure.

Example 15

Preparation of 5-benzyl-2,4-(dimorpholino) pyrimidine

A mixture of 5-benzyluracil (39.0 g, 193 mmoles) and phosphorus oxychloride (Aldrich) (280 g, 1.82 moles) was refluxed with stirring under a DRIERITE® tube for 2.5 hours. The cooled reaction mixture was slowly poured into a stirred mixture of crushed ice and diethyl ether (100 mL). After the mixture warmed to ambient temperature additional diethyl ether (200 mL) was added, and the mixture was stirred for 10 minutes. The other layer was separated, filtered to remove insoluble starting material, and then washed with saturated aqueous sodium bicarbonate (3×100 mL). Tho solution was dried over calcium chloride, filtered and spin evaporated in vacuo to give 35.43 g ( 76% yield) of the intermediate 5-benzyl-2,4-dichloropyrimidine as a syrup, which was used without further purification. A solution of crude 5-benzyl-2,4-dichloropyrimidine (9.76 g, 40.6 mmoles) and morpholine (13.0 g, 150 mmoles) in ethanol (55 mL) was stirred at ambient temperature for 21 hours. The solution was cooled in an ice-bath, and the resultant precipitate was removed by suction filtration. The filtrate was spin evaporated in vacuo to give a syrup that solidified. The solid was triturated for 3 hours with diethyl ether (200 mL) and collected by suction filtration. Recrystallization from ethanol, 2-propanol, and finally methanol gave 2.03 g (14% yield) of 5-benzyl-2,4-(dimorpholino)pyrimidine, mp 123–124° C.

Example 16 a) Preparation of ethyl 4-chloro-2-fluorophenoxyacetate

A mixture of 4-chloro-2-fluorophenol (Aldrich) (5.00 g, 33.78 mmoles), anhydrous potassium carbonate (Aldrich) (7.20 g, 52.10 mmoles), ethyl bromoacetate (Aldrich) 5.41 g 31.74 mmoles) and dry acetone (Aldrich) (80 mL) was refluxed with stirring under a DRIERITE® tube for 21 hours. The reaction was cooled, and the volatiles were removed by spin evaporation in vacuo. The white residue was partitioned between ice cold water (150 mL) and dichloromethane (150 mL).

The dichloromethane phase was separated and washed with ice cold water (2×50 mL), an ice cold solution of 5% aqueous sodium hydroxide (50 mL) and finally with ice cold water (2×50 mL). The dichloromethane solution was dried over sodium sulfate and spin evaporated in vacuo to give a quantitative yield of ethyl 4-chloro-2-fluorophenoxyacetate as a clear liquid.

Example 17

Preparation of 2-amino-5-(4-chlorophenoxy)-4-(4-(2-pivaloyloxyethyl)piperazino)pyrimidine A solution of trimethylacetyl chloride (Aldrich) (0.063 g, 0.52 mmoles) in of dry dichloromethane (3 mL) was added to a stirred, ice bath cooled solution of 2-amino-5-(4-chlorophenoxy)-4-(4-(2-hydroxyethyl)piperazino) pyrimidine (0.185 g, 0.5 mmoles) in dichloromethane (5 mL). Solid 4-dimethylaminopyridine (Aldrich) (0.061 g, 0.5 mmoles) was added to the mixture, and the resultant solution was stirred on an ice bath for 4.5 hours. The reaction solution was diluted with additional dichloromethane (50 mL) and washed with 5% aqueous sodium bicarbonate (2×25 mL) and water (2×25 mL). The organic phase was dried over sodium sulfate and spin evaporated in vacuo to give 0.15 g of a white solid. The solid was dissolved in ethyl acetate and applied to a column of silica gel 60 (230–400 mesh) prepared for flash chromatography in ethyl acetate. The column was eluted with ethyl acetate, and the solvent was spin evaporated in vacuo to give a white solid that was recrystallized from dichloromethane-hexanes to give 0.088 g (40% yield) of 2-amino-5-(4-chlorophenoxy)-4-(4-(2-pivaloyloxyethyl)piperazino)pyrimidine as white needles, mp 123–125° C.

Example 18

Preparation of 2-chloro-5-(4-methylbenzyl)-4-(4-methylpiperazino)pyrimidine

A solution of 5-benzyl-2,4-dichloropyrimidine (9.66 g, 38 mmoles), triethylamine (Aldrich) (4.15 g, 41 mmoles), and ethanol (20 mL) was stirred at ice bath temperature for 10 minutes. 1-Methylpiperazine (Aldrich) (3.83 g, 38 mmoles) in ethanol (10 mL) was added, and the reaction was stirred at ambient temperature for 16 hours. The solution was spin evaporated in vacuo at 40° C. to give a residue that was partitioned between dichloromethane (50 mL) and water (70 mL). The dichloromethane phase was separated and washed with water (2×7 mL), and finally with brine (50 mL). The dichloromethane solution was dried over sodium sulfate, filtered and applied to a column (4×20 cm) of Silica Gel 60 (230–400 mesh) that was equilibrated with dichloromethane. The column was eluted with dichloromethane (400 mL) by flash chromatography to remove impurities. The product was eluted with 2% methanol-dichloromethane, and the combined fractions were spin evaporated in vacuo to give 9.89 g (cc % yield) of 2-chloro-5-(4-methylbenzyl)-4-(4-methylpiperazino)pyrimidine.

Example 19

Preparation of 2-(2-hydroxyethoxy)ethylamino)-5-(4-methylbenzyl)-4-(4-methylpiperazino)pyrimidine A solution of 2-chloro-5-(4-methylbenzyl)-4-(4-methylpiperazino)pyrimidine (1.46 g, cc mmoles), 2-propanol (25 mL) and 2-(2-aminoethoxy)ethanol (4.79 g, 46 mmoles) was heated in a stainless steel reaction vessel at 155° C. for 16 hours. The vessel contents were spin evaporated in vacuo at 60° C. to give a residue that was partitioned between dichloromethane (35 mL) and water (150 mL). The dichloromethane phase was separated and washed with water (150 mL), and finally with brine (100 mL). The solution was dried over sodium sulfate, filtered, and spin evaporated in vacuo to give a syrup. The syrup was dissolved in 2-propanol (20 mL), 37% hydrochloric acid (15 drops) was added, and the solution was spin evaporated in vacuo. The residue was crystallized from methanol (2 mL) to give 0.34 g of 2-(2-hydroxyethoxy)ethylamino)-5-(4-methylbenzyl)-4-(4-methylpiperazino)pyrimidine as carmel colored crystals, mp 207–209° C.

The following compounds were prepared by methods similar to those of the indicated Examples.

| Chemical Name | MP° C. | Ex. No. |
|---|---|---|
| 2-Amino-4-morpholino-5-(phenoxy)pyrimidine | 188–170 | 1, 8 |
| 2-Amino-5-(4-methylphenoxy)-4-(morpholino)pyrimidine | 145–147 | 1, 8 |
| 2-Amino-5-(4-fluorophenoxy)-4-(morpholino)pyrimidine | 123–125 | 1, 8 |
| 2-Amino-5-(4-chlorophenoxy)-4-(morpholino)pyrimidine | 138–140 | 1, 8 |
| 2-Amino-5-(4-chlorobenzyloxy)-4-(morpholino)pyrimidine |  | 1, 8 |
| 2-Amino-5-(benzyloxy)-4-(morpholino)pyrimidine |  | 1, 8 |
| 2-Amino-5-(4-chlorophenoxy)-4-(2-(2-hydroxyethoxy)ethylamino)-pyrimidine HCl | 140–141 | 1, 6 |
| 2-Amino-4-(4-carbamoylpiperidino)5-(4-chlorophenoxy)-pyrimidine | 208–211 | 1, 7 |
| 2-Amino-5-(4-chlorophenoxy)-4-(piperazino)pyrimidine | 93–95 | 1, 2 |
| 2-Amino-5-(4-chlorophenoxy)-4-(4-methylpiperazino)-pyrimidine | 143–144 | 1, 5 |
| 2-Amino-5-(4-chlorophenoxy)-4-(4-ethylpiperazino)-pyrimidine | 129–131 | 1, 5 |
| 2-Amino-5-(4-chlorophenoxy)-4-(4-hydroxyethyl)piperazino)-pyrimidine | 120–135 | 1, 4 |
| 2-Amino-5-(4-fluorophenoxy)-4-(4-phenylpiperazino)-pyrimidine | 219–222 | 1, 4 |
| 2-Amino-5-(4-chlorophenoxy)-4-(4-phenylpiperazino)-pyrimidine | 186–187 | 1, 4 |
| 2-Amino-5-(4-chlorophenoxy)-4-(4-(2-pyridyl)piperazino)-pyrimidine | 123–124 | 1, 4 |
| 2-Amino-4-(4-benzylpiperazino)-5-(4-chlorophenoxy)-pyrimidine | 119–120 | 1, 4 |
| 2-Amino-5-(4-chlorophenoxy)-4-(4-formylpiperazino)-pyrimidine | 159–161 | 1, 2, 3 |
| 4-(4-Acetylpiperazino)-2-amino-5-(4-chlorophenoxy)-pyrimidine | 153–157 | 1, 2, 9 |
| 2-Amino-5-(4-chlorophenoxy)-4-(4-methoxyacetylpiperazino)-pyrimidine | 148–150 | 1, 2, 9 |
| 2-Anilino-5-(4-chlorophenoxy)-4-(morpholino)pyrimidine |  | 13, 14, 8 |
| 5-(4-Chlorophenoxy)-2-(dimethylamino)-4-(4-methylpiperazino)-pyrimidine | 165–170 | 1, 4 |
| 5-(4-Chlorophenoxy)-4-(morpholino)-2-(3-phenylureldo)-pyrimidine | 229–231 | 1, 8, 10 |
| 5-(4-Chlorophenoxy)-2,4-(dimorpholino)pyrimidine | 150–151 | 13, 14, 4 |

-continued

| Chemical Name | MP° C. | Ex. No. |
|---|---|---|
| 5-(4-Chlorophenoxy)-2-(4-methylpiperazino)-4-(morpholino)-pyrimidine HCl | 209–210 | 13, 14, 6 |
| 5-(4-Chlorophenoxy)-4-(4-methylpiperazino)-2-(morpholino)-pyrimidine | 259–260 | 13, 14, 5 |
| 5-(4-Chlorophenoxy)-4-[4-(2-hydroxyethyl)piperazino]-2-(morpholino)-pyrimidine | | 13, 14, 4 |
| 2-Amino-5-benzyl-4-(morpholino)pyrimidine | 206–207 | 1, 8 |
| 2-Amino-5-benzyl-4-(dimethylamino)pyrimidine | 181–182 | 1, 11 |
| 2-Amino-5-(4-methoxybenzyl)-4-(morpholino)pyrimidine | 136–137 | 1, 8 |
| 5-Benzyl-4-[2-(2-hydroxyethoxy)ethylamino]pyrimdine | 86–87 | 15, 12 |
| 2-Amino-5-benzyl-4-(4-hydroxypiperidino)pyrimidine | 145–146 | 1, 4 |
| 2-Amino-5-benzyl-4-(4-methylpiperazinoamino)-pyrimidine | 184–185 | 1, 4 |
| 2-Amino-5-benzyl-4-(4-carbamoylpiperidino)pyrimidine | 217–218 | 1, 7 |
| 2-Amino-5-benzyl-4-(4-methylpiperazino)pyrimidine | 174–175 | 1, 4 |
| 2-Amino-5-benzyl-4-(4-hydroxyethylpiprazino)-pyrimidine | 161–162 | 1, 4 |
| 5-Benzyl-2,4-bis(4-methylpiperazino)pyrimidine | | 15 |
| 5-Benzyl-2,4-(dimorpholino)pyrimidine | 123–124 | 15 |
| 5-Benzyl-2-dimethylamino-4-(4-methylpiperazino)-pyrimidine HCl | | 1, 6 |
| 2-Amino-5-(4-methylbenzyl)-4-(4-methylpiperazino)-pyrimidine | 185–186 | 1, 5 |
| 2-Amino-4-(4-ethylpiperazino)-5-(4-methylbenzyl)-pyrimidine | 115–116 | 1, 5 |
| 2-Amino-4-(4-hydroxyethylpiperazino)-5-(4-methylbenzyl)-pyrimidine | 122–124 | 1, 4 |
| 2-Amino-4-(4-hydroxypiperazino)-5-(4-methylbenzyl)-pyrimidine | 153–154 | 1, 4 |
| 2-Amino-5-(4-chlorobenzyl)-4-(morpholino)pyrimidine | 181–183 | 1, 8 |
| 2-Amino-4-[2-(2-hydroxyethyl)ethylamino]-5-(4-chlorobenzyl)-pyrimidine | 59–60 | 1, 5 |
| 2-Amino-5-(4-chlorobenzyl)-4-(4-methylpiperazino)-pyrimidine | 194–195 | 1, 5 |
| 2-Amino-5-(4-chlorobenzyl)-4-(4-ethylpiperazino)-pyrimidine | 157–161 | 1, 5 |
| 2-Amino-5-(4-chlorobenzyl)-4-(4-hydroxyethylpiperazino)-pyrimidine | 98–99 | 1, 4 |
| 2-Amino-5-(4-chlorobenzyl)-4-(4-hydroxypiperazino)-pyrimidine | 183–184 | 1, 4 |
| 2-Amino-5-(4-methoxybenzyl)-4-(4-methylpiperazino)-pyrimidine | 157–158 | 1, 5 |
| 2-Amino-5-(4-hydroxybenzyl)-4-(4-methylpiperazino)-pyrimidine HCl | 155–156 | 1, 6 |
| 2-Amino-4-(4-methylpiperazino)-5-(isopropylbenzyl)-pyrimidine | 178–181 | 1, 5 |
| 2-Amino-4-(4-ethylpiperazino)-5-(4-isopropylbenzyl)-pyrimidine | 149–150 | 1, 5 |
| 2-Amino-4-(4-hydroxyethylpiperazino)-5-(4-isopropylbenzyl)-pyrimidine | 136–137 | 1, 4 |
| 2-Amino-4-(4-hydroxypiperazino)-5-(4-isopropylbenzyl)-pyrimidine | 146–148 | 1, 4 |
| 2-Amino-4-(4-methylpiperazino)-5-(3,4,5-trimethoxybenzyl)-pyrimidine | 190–192 | 1, 5 |
| 2-Amino-4-(4-ethylpiperazino)-5-(3,4,5-trimethoxybenzyl)-pyrimidine | 160–161 | 1, 5 |
| 2-Amino-4-(4-hydroxyethylpiperazino)-5-(3,4,5-trimethoxybenzyl)-pyrimidine | 155–157 | 1, 4 |
| 2-Amino-4-(4-hydroxypiperazino)-5-(3,4,5-trimethoxybenzyl)-pyrimidine | 164–165 | 1, 4 |
| 2-Amino-4-(4-methylpiperazino)-5-(4-[4-chlorobenzyloxy]benzyl)-pyrimidine | 171–172 | 1, 5 |
| 2-Amino-4-(4-ethylpiperazino)-5-(4-[4-chlorobenzyloxy]benzyl)-pyrimidine | 149–150 | 1, 5 |
| 2-Amino-4-(4-hydroxyethylpiperazino)-5-(4-[4-chlorobenzyloxy]benzyl)-pyrimidine | 155–156 | 1, 4 |
| 2-Amino-4-(4-methylpiperazino)-5-((3-pyridyl)methyl)-pyrimidine | 174–175 | 1, 5 |
| 2-Amino-4-(4-ethylpiperazino)-5-([3-pyridyl]methyl]-pyrimidine | 160–161 | 1, 5 |
| 2-Amino-4-(4-hydroxyethylpiperazino)-5-([3-pyridyl]methyl)-pyrimidine | 144–145 | 1, 4 |
| 4-Anilino-2-methyl-5-(phenethyl)pyrimidine | 133–134 | 1, 4 |
| 4-Benzylamino-2-methyl-5(phenethyl)pyrimidine | 116–117 | 1, 4 |
| 4-[2-(2-Hydroxyethoxy)ethylamino]-2-methyl-5-(phenethyl)-pyrimidine | 85–86 | 1, 4 |
| 2-Methyl-4-morpholino-5-(phenethyl)pyrimidine | 48–49 | 1, 8 |

-continued

| Chemical Name | MP° C. | Ex. No. |
|---|---|---|
| 2,4-Dimorpholino-5-(phenethyl)pyrimidine | 70–72 | 15 |
| 2-Amino-4-morpholino-5-(phenethyl)pyrimidine | 116–117 | 1, 8 |
| 4-Morpholino-5-(phenethyl)pyrimidine HCl | 243–244 | 15, 12 |
| 2-Amino-5-(4-methoxyphenethyl)-4-(morpholino)pyrimidine | 123–124 | 1, 8 |
| 2-Amino-4-morpholino-5-(phenylpropyl)pyrimdine | 105–106 | 1, 8 |
| 2-Amino-4-morpholino-5-(phenyl)pyrimdine | 174–175 | 1, 8 |
| 2-Amino-5-(4-fluorophenyl)-4-(morpholino)pyrimidine | 202–203 | 1, 8 |
| 2-Amino-5-(4-chlorophenyl)-4-(morpholino)pyrimidine | 235–237 | 1, 8 |
| 2-Amino-5-(4-bromophenyl)-4-(morpholino)pyrimidine | 228–229 | 1, 8 |
| 2-Amino-5-(4-ethylphenoxy)-4-(4-methylpiperazino)-pyrimidine | 118–119 | 16, 1, 5 |
| 2-Amino-5-(4-dichlorophenoxy)-4-(4-methylpiperazino)-pyrimidine | 142–145 | 16, 1, 5 |
| 2-Amino-5-(4-chloro-2-methylphenoxy)-4-(4-methylpiperazino)-pyrimidine | 114–115 | 16, 1, 5 |
| 2-Amino-5-(3-chlorophenoxy)-4-(4-(2-hydroxyethyl)piperazino)-pyrimidine | 128–129 | 16, 1, 5 |
| 2-Amino-5-(2-chlorophenoxy)-4-(4-(2-hydroxyethyl)piperazino)-pyrimidine | 111–112 | 16, 1, 4 |
| 2-Amino-5-(4-bromophenoxy)-4-(4-(2-hydroxyethyl)piperazino)-pyrimidine | 130–131 | 16, 1, 4 |
| 2-Amino-5-(4-fluorophenoxy)-4-(4-(2-hydroxyethyl)piperazino)-pyrimidine | 111–112 | 16, 1, 4 |
| 2-Amino-5-(3-fluorophenoxy)-4-(4-(2-hydroxyethyl)piperazino)-pyrimidine | | |
| 2-Amino-4-(4-(2-hydroxyethyl)piperazino)-5-(4-trifluoromethyl-phenoxy)pyrimidine | 157–158 | 16, 1, 4 |
| 2-Amino-4-(4-(2-hydroxyethyl)piperazino)-5-(4-methylphenoxy)-pyrimidine | 98–99 | 16, 1, 4 |
| 2-Amino-4-(4-(2-hydroxyethyl)piperazino)-5-(3-methylphenoxy)-pyrimidine | 114–115 | 16, 1, 4 |
| 2-Amino-4-(4-(2-hydroxyethyl)piperazino)-5-(2-methylphenoxy)-pyrimidine | 113–114 | 16, 1, 4 |
| 2-Amino-5-(4-ethylphenoxy)-4-(4-(2-hydroxyethyl)piperazino)-pyrimidine | 105–107 | 16, 1, 4 |
| 2-Amino-4-(4-(2-hydroxyethyl)piperazino)-5-(4-isopropylphenoxy)-pyrimidine | 118–119 | 16, 1, 4 |
| 2-Amino-5-(4-butylphenoxy)-4-(4-(2-hydroxyethyl)piperazino)-pyrimidine | 139–140 | 16, 1, 4 |
| 2-Amino-4-(4-(2-hydroxyethyl)piperazino)-5-(4-methoxyphenoxy)-pyrimidine | 94–95 | 16, 1, 4 |
| 2-Amino-4-(4-(2-hydroxyethyl)piperazino)-5-(3-methoxyphenoxy)-pyrimidine | 123–124 | 16, 1, 4 |
| 2-Amino-4-(4-(2-hydroxyethyl)piperazino)-5-(2-methoxyphenoxy)-pyrimidine | 114–115 | 16, 1, 4 |
| 2-Amino-4-(4-(2-hydroxyethyl)piperazino)-5-(4-trifluoromethoxy)phenoxy)-pyrimidine | 131–132 | 16, 1, 4 |
| 2-Amino-5-(2,4-dichlorophenoxy)-4-(4-(2-hydroxyethyl)piperazino)-pyrimidine | 170–173 | 16, 1, 4 |
| 2-Amino-5-(2,3-difluorophenoxy)-4-(4-(2-hydroxyethyl)piperazino)-pyrimidine | 117–118 | 16, 1, 4 |
| 2-Amino-5-(2,4-difluorophenoxy)-4-(4-(2-hydroxyethyl)piperazino)-pyrimidine | 110–111 | 16, 1, 4 |
| 2-Amino-5-(2,6-difluorophenoxy)-4-(4-(2-hydroxyethyl)piperazino)-pyrimidine | 114–115 | 16, 1, 4 |
| 2-Amino-5-(3,5-difluorophenoxy)-4-(4-(2-hydroxyethyl)piperazino)-pyrimidine | 137–138 | 16, 1, 4 |
| 2-Amino-5-(4-chloro-2-fluorophenoxy)-4-(4-(2-hydroxyethyl)piperazino)-pyrimidine | 129–133 | 16, 1, 4 |
| 2-Amino-5-(4-chloro-4-fluorophenoxy)-4-(4-(2-hydroxyethyl)piperazino)-pyrimidine | 129–133 | 16, 1, 4 |
| 2-Amino-5-(4-chloro-2-methylphenoxy)-4-(4-(2-hydroxyethyl)piperazino)-pyrimidine | 171–172 | 16, 1, 4 |
| 2-Amino-5-(4-chlorophenoxy)-4-(4-(2-pivaloyloxyethyl)piperazino)-pyrimidine | 123–125 | 1, 4, 17 |
| 2-Amino-4-(4-butyrylpiperazino)-5-(4-chlorophenoxy)-pyrimidine | 132–142 | 1, 5, 9 |
| 2-Amino-5-(4-chlorophenoxy)-4-(4-phenoxyacetylpiperazino)-pyrimidine | 126–127 | 1, 5, 9 |
| 2-Amino-4-(4-benzolypiperazino)-5-(4-chlorophenoxy)-pyrimidine | 162–167 | 1, 5, 9 |
| 2-Amino-5-(4-chlorophenoxy)-4-(4-ethoxycarbonylpiperazino)-pyrimidine | 121–123 | 1, 5, 9 |
| 2-Amino-5-(4-chlorophenoxy)-4-(4-phenoxycarbonylpiperazino)-pyrimidine | 128–130 | 1, 5, 9 |
| 2-Amino-5-(4-chlorophenoxy)-4-(4-methoxydicarbonylpiperazino)-pyrimidine HCl | 182–185 | 1, 5, 9 |

-continued

| Chemical Name | MP° C. | Ex. No. |
|---|---|---|
| 2-Amino-4-(4-(3-carbamoylpropionyl)piperazino)-5-(4-chlorophenoxy)-pyrimidine | 115–119 | 1, 5, 9 |
| 2-Amino-4-(4-(3-carboxypropionyl)piperazino)-5-(4-chlorophenoxy)-pyrimidine | 117–119 | 1, 5, 9 |
| 2-Amino-5-(4-chlorophenoxy)-4-(4-(methylsulfonyl)piperazino)-pyrimidine | 65–70 | 1, 5, 9 |
| 2-Amino-5-(4-chlorophenoxy)-4-(4-phenylsulfonyl)piperazino)-pyrimidine | <60 | 1, 5, 9 |
| 5-(4-Chlorophenoxy)-4-(4-methylpiperazino)-2-(1-pyrrolidinyl)-pyrimidine | 112–113 | 13, 14, 5 |
| 1-(Anilino)-5-(4-chlorophenoxy)-4-(4-methylpiperazino)-pyrimidine | | 13, 14, 5 |
| 5-(4-Chlorophenoxy)-2-(4-fluoroanilion)-4-(4-methylpiperazino)-pyrimidine 2HCl | 267–268 | 13, 14, 6 |
| 2-(Benzylamine)-5-(4-chlorophenoxy)-4-(4-methylpiperazino)-pyrimidine | 93–94 | 13, 14, 5 |
| 2,4-Bis(4-ethylpiperazino)-5-(4-chlorophenoxy)-pyrimidine 2HCl | 267–268 | 13, 14, 6 |
| 5-(4-Chlorophenoxy)-4-(4-(2-hydroxyethyl)piperazino)-2-(isopropylamino)-pyrimidine 2HCl | 254–256 | 13, 14, 6 |
| 5-(4-Chlorophenoxy)-2-((2-hydroxyethyl)amino)-4-(4-(2-hydroxyethyl)-piperazino)pyrimidine maleate | 155–164 | 13, 14, 6 |
| 5-(4-Chlorophenoxy)-2-(2-(2-hydroxyethy)ethylamino)-4-(4-(2-hydroxyethyl)piperazino)pyrimidine HCl | 134–135 | 13, 14, 6 |
| 2-(Anilino)-5-(4-chlorophenoxy)-4-(4-(2-hydroxyethyl)piperazino)-pyrimidine | 122–123 | 13, 14, 4 |
| 5-(4-Chlorophenoxy)-2-(4-fluoroanilino)-4-(4-(2-hydroxyethyl)piperazino)-pyrimidine HCl | 192–195 | 13, 14, 6 |
| 5-(4-Chlorophenoxy)-4-(4-(2-hydroxyethyl)piperazino)-2-(4-methylanilino)-pyrimidine | 155–158 | 13, 14, 4 |
| 5-(4-Chlorophenoxy)-4-(4-(2-hydroxyethyl)piperazino)-2-(1-pyrrolidinyl)-pyrimidine | 110–111 | 13, 14, 4 |
| 5-(4-Chlorophenoxy)-4-(4-(2-hydroxyethyl)piperazino)-2-(piperidino)-pyrimidine 2HCl | 227–232 | 13, 14, 6 |
| 5-(4-Chlorophenoxy)-4-(4-(2-hydroxyethyl)piperazino)-2-(4-hydroxypiperidino)pyrimidine 2HCl | 262 (dec) | 13, 14, 6 |
| 5-(4-Chlorophenoxy)-4-(4-(2-hydroxyethyl)piperazino)-2-(4-phenylpiperazino)pyrimidine 3HCl | 236–245 (dec) | 13, 14, 6 |
| 5-(4-Chlorophenoxy)-4-(4-(2-hydroxyethyl)piperazino)-2-(4-methylpiperazino)pyrimidine 3HCl | 280 (dec) | 13, 14, 6 |
| 5-(4-Chlorophenoxy)-2-(4-ethylpiperazino)-4-(4-(2-hydroxyethyl)piperazino)pyrimidine 3HCl | 245–248 | 13, 14, 6 |
| 2,4-Bis(4-(2-hydroxyethyl)piperazino)-5-(4-chlorophenoxy)-pyrimidine 2HCl | 243–244 | 13, 14, 6 |
| 2-Chloro-5-(4-chlorophenoxy)-4-(4-(2-hydroxyethyl)piperazino)-pyrimidine | 95–96 | 15 |
| 5-(4-Chlorophenoxy)-4-(4-(2-hydroxyethyl)piperazino)-pyrimidine HCl | 180–181 | 1, 4 |
| 5-(4-Chlorophenoxy)-4-(4-methylpiperazino)pyrimidine | 155–157 | 1, 5 |
| 2-Amino-5-(4-chlorophenyl)-4-(4-(2-hydroxyethyl)piperazino)-pyrimidine | 203–204 | 1, 4 |
| 2-Amino-5-(4-chlorophenyl-4-(4-methylpiperazino)-pyrimdine | 185–186 | 1, 5 |
| 2-Amino-5-(4-fluorophenyl-4-(4-methylpiperazino)-pyrimdine | 182–184 | 1, 5 |
| 2-Amino-4-(4-hydroxyethylpiperazino)-5-(4-trifluoromethylbenzyl)-pyrimidine | 154–155 | 1, 4 |
| 2-(4-Carbamolypiperidino)-5-(4-methylbenzyl)-4-(4-methylpiperazino)pyrimidine | 179–180 | 18, 19 |
| 2-(2-Hydroxyethoxy)ethylamino)-5-(4-methylbenzyl)-4-(4-methylpiperazino)-pyrimidine | 207–209 | 18, 19 |
| 2-Amino-5-(4-chlorophenethyl)-4-(4-methylpiperazino)-pyrimidine | 159–160 | 1, 5 |
| 2-Amino-5-(4-chlorophenethyl)-4-(4-(2-hydroxethyl)piperazino)-pyrimidine | 123–124 | 1, 4 |
| 2-Amino-5-(4-chlorobenzyloxy)-4-(4-methylpiperazino)-pyrimidine | 167–168 | 16, 1, 5 |
| 2-Amino-5-(4-chlorobenzyloxy)-4-(4-(2-hydroxyethyl)piperazino)-pyrimidine | 178–179 | 16, 1, 4 |
| 2-Amino-5-(4-chlorophenoxy)-4-(4-hydroxypiperidino)-pyrimidine | 146–147 | 1, 5 |
| 2-Amino-4-(4-hydroxypiperazino)-5-(4-methylphenoxy)-pyrimidine | 148–151 | 1, 5 |
| 2-Amino-5-(2,4-dichlorophenoxy)-4-(4-hydroxypiperidino)-pyrimidine HCl | 247–252 | 1, 6 |
| 5-(4-Chlorophenoxy)-4-(4-hydroxypiperidino)-2-morpholino-pyrimidine HCl | | 13, 14, 6 |

-continued

| Chemical Name | MP° C. | Ex. No. |
|---|---|---|
| 2-Amino-5-(4-chlorophenoxy)-4-(3-(hydroxymethyl)piperidino)-pyrimidine | 172–173 | 1, 5 |
| 2-Amino-5-(4-chlorophenoxy)-4-(2-(2-hydroxyethyl)piperidino)-pyrimidine | 153–154 | 1, 4 |
| 5-(4-Chlorophenoxy)-4-(2-(2-hydroxyethoxy)ethylamino)-2-morpholinopyrimidine HCl | 160–163 | 13, 14, 6 |
| 2-Anilino-4-(4-hydroxypiperidino)-5-(4-methylbenzyl)-pyrimidine | 135–136 | 18, 19 |
| 2,4-Bis-(4-Hydroxypiperidino)-5-(4-methylbenzyl)-pyrimidine HCl | 201–202 | 15 |
| 4-(4-Hydroxypiperidino)-5-(phenethyl)pyrimidine HCl | wax | 15, 12 |
| 2-Amino-4-(4-carbamolypiperidino)-5-(4-chlorophenethyl)-pyrimidine | 205–206 | 1, 5 |

Representative Pharmaceutical Compositions

In the following Examples, the "Active Ingredient" may be any compound of Formula I or a pharmaceutically acceptable salt thereof.

Example A

Tablet Composition

| | mg/tablet |
|---|---|
| (a) Active Ingredient | 250 |
| (b) Lactose B.P. | 210 |
| (c) Povidone B.P. | 15 |
| (d) Sodium Starch Glyollate | 20 |
| (e) Magnesium Stearate | 5 |

The composition is prepared by wet granulation of the ingredients with a solution of povidons, followed by addition of magnesium stearate and compression.

Example B

Capsule Composition

A capsule composition is prepared by admixing the ingredients and filling into a two-part hard gelatin capsule.

| | mg/capsule |
|---|---|
| (a) Active Ingredient | 250 |
| (b) Lactose B.P. | 143 |
| (c) Sodium Starch Glycollate | 25 |
| (d) Magnesium Stearate | 2 |

Example C

Injectable Composition

| | |
|---|---|
| (a) Active Ingredient | 0.200 g |
| (b) Hydrochloric Acid Solution 0.1 M or Sodium Hydroxide Solution 0.1 M to pH | 4.0 to 7.0 |
| (c) Sterile Water q.s. to | 10 ml |

The active ingredient is dissolved in most of the water (35°–40° C.) and the pH is adjusted to between 4.0 and 7.0.

The batch is then made up to volume with sterile water and filtered through a sterile micropore filter into a sterile amber glass vial (type 1) and sealed with sterile closures and overseals.

Neurotrophic Activity

Screen for NGF-like Activity:

Cultured PC12 cells (rat adrenal pheochromocytoma from ATCC) have receptors for NGF. Responses include promotion of neurite outgrowth and elevation of choline acetyltransferase (ChAT) (L. A. Greene and A. S. Tischler, Cell Neurobiol., 3, 373 (1982)).

The following assay is substantially as described in H L White and P W Scates, Neurochem. Res., 16, 63 (1991). PC12 cells were cultured at 37° C. in DMEM supplemented with fetal bovine serum, horse serum, glutamine, penicillin, streptomycin and non-essential amino acids. Cultures were split 1:4 every 4 or 5 days. Exponentially dividing cells were plated in fresh medium on collagen-coated 12-well plastic dishes. After allowing one day for cell attachment, the medium was replaced with low serum medium, with or without test compounds and also with or without a limiting concentration of NGF, with each condition in triplicate. The medium may contain up to 0.1% ethanol, which was used as a solvent for most compounds being tested. Cells were examined daily for morphological changes using an Olympus IMT-2 inverted research microscope. After 2 days incubation with test compounds, cells and media were transferred to 1.5 mL Eppendorf tubes. Aliquots of 20 uL were reserved for cell counting and viability determination by trypan blue exclusion. The remaining cell suspensions were centrifuged, and the cell pellets were washed once in serum-free medium and finally resuspended in 30 uL of distilled water containing eserine, an inhibitor of acetylcholinesterase. The suspensions were stored at −80° C. until they were assayed for choline acetyltransferase. Compounds are judged NGF-like in this primary screen if they (1) increase the activity of choline acetyltransferase, (2) enhance NGF-stimulated neurite outgrowth or (3) potentiate and appear additive with the action of NGF itself.

Choline Acetyltransferase (ChAT) Assays

Resuspended cells were lysed by 3 freeze-thaw cycles and 2×5 seconds of sonication, using a Heat Systems Ultronic Model W385 with a cup horn attachment. ChAT in cell lysates was determined by the ion exchange procedure of White and Scates (H. L. White and P. W. Scates, Neurochem. Res., 16, 63 (1991)). The assay involves incubation of cell lysate in a total assay volume of 50 uL containing final concentrations (mM) of potassium phosphate (10), EDTA (0.02), sodium chloride (200), eserine (0.12), choline (0.5), and 0.2 uCi of [$^{14}$C]acetyl-coenzyme A (0.04). Following a 20 minute incubation at 37° C., assay mixtures were applied to 0.5×3 cm columns of Bio-Rad AG1-X8 resin (chloride form), and the product, [$^{14}$C]acetylcholine, was eluted directly into scintillation vials with 1.5 mL of distilled water.

In Vitro Activity Data

The compounds according to the invention (1) increased the activity of choline acetyltransferase, (2) enhanced NGF-stimulated neurite outgrowth and/or (3) potentiated or appeared additive with the action of NGF itself. Compounds having especially potent activities: 2-Amino-5-(4-chlorophenoxy)-4-(4-methylpiperazino)pyrimidine; 2-Amino-5-(4-chlorobenzyl)-4-(4-hydroxypiperidino)pyrimidine; 2-Amino-4-[2-(2-hydroxyethyl)ethylamino]-5-(4-chlorobenzyl)pyrimidine; and 2-Amino-5-(4-chlorophenoxy)-4-(4-formylpiperazino)pyrimidine.

What is claimed is:

1. A compound of Formula I

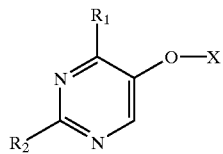

wherein:

$R_1$ is hydroxyC1–C6alkyloxyC1–6alkylamino, morpholino, piperidino, piperazino, piperazinoamino, homopiperazino, homopiperidino, or homomorpholino, wherein C or N atoms of $R_1$ may be substituted with one or more substituents selected from the group consisting of:
$NR_4R_5$ (wherein $R_4$ and $R_5$ may be the same or different and are H, C1–6alkyl, hydroxyC1–6alkyl, C3–8cycloalkyl, C6–10aryl, C6–10arylC1–6alkyl, C1–6alkoxy, C6–10aryloxy or C6–10arylC1–6alkoxy);
$NR_4R_5$carbonyC1–C6alkyl (wherein $R_4$ and $R_5$ may be the same or different);
OH;
CN;
C1–6alkyl;
C2–7alkenyl;
C2–7alkynyl;
C6–10aryl;
C6–10heteroaryl;
hydroxyC1–6alkyl;
dihydroxyC1–6alkyl;
C1–6alkoxy;
C1–6aryloxy;
C6–10heteroaryloxy;
hydroxyC1–6alkoxy;
C1–6alkoxyC1–6alkyl;
C6–10aryloxyC1–6alkyl;
C6–10heteroaryloxyC1–6alkyl;
C3–8cycloalkyl;
C6–10arylC1–6alkyl;
C6–10heteroarylC1–6alkyl;
C6–10arylC1–6alkoxy; and
C6–10heteroarylC1–6alkoxy;

$R_2$ is selected from the group consisting of:
H;
halogen;
$NR_7R_8$ (wherein $R_7$ and $R_8$ may be the same or different and are H, C1–6alkyl, C1–6alkyloxy, C1–6alkyl, C3–8cycloalkyl, C6–10arylC6–10arylC1–6alkyl, C1–6alkoxy, C6–10aryloxy, C6–C10arylC1–6alkoxy, or C(O)C1–6alkyl, each of which may be optionally substituted with one or more substituents selected from the group consisting of OH, halogen and C1–6alkyl);
pyrrolidino;
piperidino;
hydroxypiperidino;
heptamethyleneimino;
piperazino;
N-substituted piperazino (wherein the substituent may be C1–6alkyl, hydroxyC1–6alkyl, C6–10aryl, C6–10arylC1–6alkyl or C6–10heteroaryl);
homopiperazino;
N-substituted homopiperazino (wherein the substituent may be C1–6alkyl, hydroxyC1–6alkyl, C6–10aryl, C6–10arylC1–6alkyl or C6–10heteroaryl);
morpholino;
homomorpholino; and
C-substituted piperidino (wherein the substituent may be C1–6alkyl, hydroxyC1–6alkyl, C6–10aryl, C6–10arylC1–6alkyl or C6–10heteroaryl);

X is a C6–10 aryl ring optionally substituted with one or more suitable substituents for an aryl ring selected from the group consisting of:
halogen;
C1–6alkyl;
C2–7alkenyl;
C2–7alkynyl;
C6–10aryl;
C6–10heteroaryl;
OR (wherein R is H, C1–6alkyl, C3–8cycloalkyl, C6–10aryl, or C6–10arylC1–6alkyl);
$NR_9R_{10}$ (wherein $R_9$ and $R_{10}$ may be the same or different and are H, C1–6alkyl, C3–8cycloalkyl, C6–10aryl, or C6–10arylC1–6alkyl);
NROR;
$C(O)NR_9R_{10}$;
C(O)OR;
C(O)R;
$NRC(O)NR_9R_{10}$;
NRC(O)R;
NRC(O)OR;
CR(OH)R;
OC(O)R;
$S(O)_nR$, wherein R is other than H and n is 0, 1, or 2;
$NRS(O)_mR$, wherein R is other than H and m is 1 or 2;
$S(O)_2NR_9R_{10}$;
$NO_2$;
CN;
$CF_3$; and
$OCF_3$;

and pharmaceutically acceptable esters, amides, salts and solvates thereof.

2. A compound according to claim 1 wherein X is substituted phenyl.

3. A compound according to claim 1 wherein $R_1$ is 4-(2-hydroxyethyl)piperazino or 2-(2-hydroxyethoxy)ethylamino, X is substituted phenyl, and $R_2$ is $NH_2$.

4. A compound of formula IA

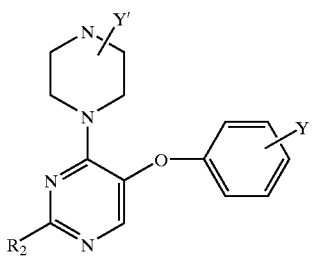

wherein
R$_2$ is selected from the group consisting of NH2, NHC1–6alkyl, NHC2H4OC2H4OC2H4OH,

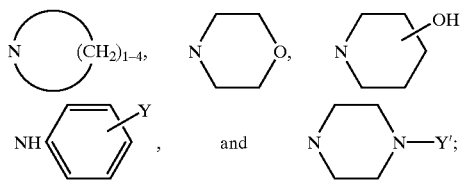

Y is any suitable substituent for an aryl ring;
Y' is selected from the group consisting of H, CH3, CH2CH3, CH2CH2OH, C(O)R, S(O)2R and C6H5;
R is selected from the group consisting of H, C1–6alkyl, C3–8cycloalkyl, C6–C10aryl and C6–C10arylC1–6alkyl;
and pharmaceutically acceptable esters, amides, salts and solvates thereof.

5. A compound of formula IB

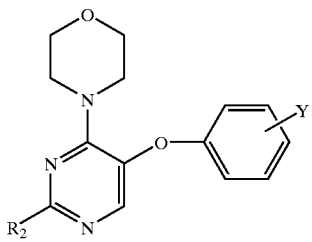

wherein
R$_2$ is selected from the group consisting of NH2, NHC1–6alkyl, NHC2H4OC2H4OC2H4OH,

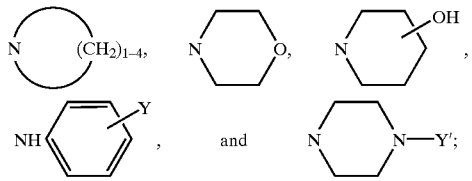

Y is any suitable substituent for an aryl ring;
Y' is selected from the group consisting of H, CH3, CH2CH3, CH2CH2OH, C(O)R, S(O)2R and C6H5;
R is selected from the group consisting of H, C1–6alkyl, C3–8cycloalkyl, C6–C10aryl and C6–C10arylC1–6alkyl;
and pharmaceutically acceptable esters, amides, salts and solvates thereof.

6. A compound of formula IC

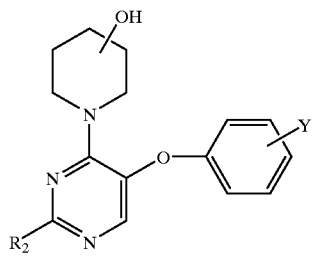

wherein
R$_2$ is selected from the group consisting of NH2, NHC1–6alkyl, NHC2H4OC2H4OC2H4OH,

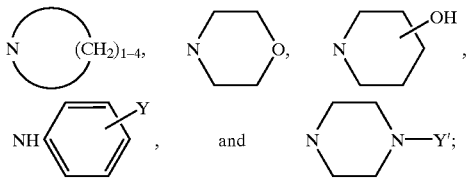

Y is any suitable substituent for an aryl ring;
Y' is selected from the group consisting of H, CH3, CH2CH3, CH2CH2OH, C(O)R, S(O)2R and C6H5;
R is selected from the group consisting of H, C1–6alkyl, C3–8cycloalkyl, C6–C10aryl and C6–C10arylC1–6alkyl;
and pharmaceutically acceptable esters, amides, salts and solvates thereof.

7. A compound of formula ID

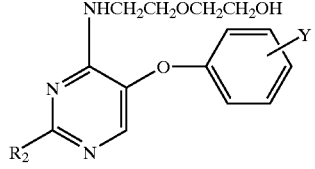

wherein
R$_2$ is selected from the group consisting of NH2, NHC1–6alkyl, and NHC2H4OC2H4OC2H4OH;
Y is any suitable substituent for an aryl ring;
and pharmaceutically acceptable esters, amides, salts and solvates thereof.

8. A compound according to claim 1 selected from:
2-Amino-4-morpholino-5-(phenoxy)pyrimidine;
2-Amino-5-(4-methylphenoxy)-4-(morpholino)pyrimidine;
2-Amino-5-(4-fluorophenoxy)-4-(morpholino)pyrimidine;
2-Amino-5-(4-chlorophenoxy)-4-(morpholino)pyrimidine;
2-Amino-5-(4-chlorophenoxy)-4-(2-(2-hydroxyethoxy) ethylamino)pyrimidine;
2-Amino-4-(4-carbamoylpiperidino)-5-(4-chlorophenoxy) pyrimidine;
2-Amino-5-(4-chlorophenoxy)-4-(piperazino)pyrimidine;
2-Amino-5-(4-chlorophenoxy)-4-(4-methylpiperazino) pyrimidine;
2-Amino-5-(4-chlorophenoxy)-4-(4-ethylpiperazino) pyrimidine;
2-Amino-5-(4-chlorophenoxy)-4-(4-(2-hydroxyethyl) piperazino)pyrimidine;
2-Amino-5-(4-fluorophenoxy)-4-(4-phenylpiperazino) pyrimidine;

2-Amino-5-(4-chlorophenoxy)-4-(4-phenylpiperazino)pyrimidine;
2-Amino-5-(4-chlorophenoxy)-4-(4-(2-pyridyl)piperazino)pyrimidine;
2-Amino-4-(4-benzylpiperazino)-5-(4-chlorophenoxy)pyrimidine;
2-Amino-5-(4-chlorophenoxy)-4-(4-formylpiperazino)pyrimidine;
4-(4-Acetylpiperazino)-2-amino-5-(4-chlorophenoxy)pyrimidine;
2-Amino-5-(4-chlorophenoxy)-4-(4-methoxyacetylpiperazino)pyrimidine;
2-Anilino-5-(4-chlorophenoxy)-4-(morpholino)pyrimidine;
5-(4-Chlorophenoxy)-2-(dimethylamino)-4-(4-methylpiperazino)pyrimidine;
5-(4-Chlorophenoxy)-4-morpholino-2-(3-phenylureido)pyrimidine;
5-(4-Chlorophenoxy)-2,4-(dimorpholino)pyrimidine;
5-(4-Chlorophenoxy)-2-(4-methylpiperazino)-4-(morpholino)pyrimidine;
5-(4-Chlorophenoxy)-4-(4-methylpiperazino)-2-(morpholino)pyrimidine;
5-(4-Chlorophenoxy)-4-[4-(2-hydroxyethyl)piperazino]-2-(morpholino)pyrimidine;
2-Amino-5-(4-ethylphenoxy)-4-(4-methylpiperazino)pyrimidine;
2-Amino-5-(2,4-dichlorophenoxy)-4-(4-methylpiperazino)pyrimidine;
2-Amino-5-(4-chloro-2-methylphenoxy)-4-(4-methylpiperazino)pyrimidine;
2-Amino-5-(3-chlorophenoxy)-4-(4-(2-hydroxyethyl)piperazino)pyrimidine;
2-Amino-5-(2-chlorophenoxy)-4-(4-(2-hydroxyethyl)piperazino)pyrimidine;
2-Amino-5-(4-bromophenoxy)-4-(4-(2-hydroxyethyl)piperazino)pyrimidine;
2-Amino-5-(4-fluorophenoxy)-4-(4-(2-hydroxyethyl)piperazino)pyrimidine;
2-Amino-5-(3-fluorophenoxy)-4-(4-(2-hydroxyethyl)piperazino)pyrimidine;
2-Amino-4-(4-(2-hydroxyethyl)piperazino)-5-(4-trifluoromethylphenoxy)pyrimidine;
2-Amino-4-(4-(2-hydroxyethyl)piperazino)-5-(4-methylphenoxy)pyrimidine;
2-Amino-4-(4-(2-hydroxyethyl)piperazino)-5-(3-methylphenoxy)pyrimidine;
2-Amino-4-(4-(2-hydroxyethyl)piperazino-5-(2-methylphenoxy))pyrimidine;
2-Amino-5-(4-ethylphenoxy)-4-(4-(2-hydroxyethyl)piperazino)pyrimidine;
2-Amino-4-(4-(2-hydroxyethyl)piperazino)-5-(4-isopropylphenoxy)pyrimidine;
2-Amino-5-(4-butylphenoxy)-4-(4-(2-hydroxyethyl)piperazino)pyrimidine;
2-Amino-4-(4-(2-hydroxyethyl)piperazino)-5-(4-methoxyphenoxy)pyrimidine;
2-Amino-4-(4-(2-hydroxyethyl)piperazino)-5-(3-methoxyphenoxy)pyrimidine;
2-Amino-4-(4-(2-hydroxyethyl)piperazino)-5-(2-methoxyphenoxy)pyrimidine;
2-Amino-4-(4-(2-hydroxyethyl)piperazino)-5-(4-(trifluoromethoxy)phenoxy)pyrimidine;
2-Amino-5-(2,4-dichlorophenoxy)-4-(4-(2-hydroxyethyl)piperazino)pyrimidine;
2-Amino-5-(2,3-difluorophenoxy)-4-(4-(2-hydroxyethyl)piperazino)pyrimidine;
2-Amino-5-(2,4-difluorophenoxy)-4-(4-(2-hydroxyethyl)piperazino)pyrimidine;
2-Amino-5-(2,6-difluorophenoxy)-4-(4-(2-hydroxyethyl)piperazino)pyrimidine;
2-Amino-5-(3,5-difluorophenoxy)-4-(4-(2-hydroxyethyl)piperazino)pyrimidine;
2-Amino-5-(4-chloro-2-fluorophenoxy)-4-(4-(2-hydroxyethyl)piperazino)pyrimidine;
2-Amino-5-(2-chloro-4-fluorophenoxy)-4-(4-(2-hydroxyethyl)piperazino)pyrimidine;
2-Amino-5-(4-chloro-2-methylphenoxy)-4-(4-(2-hydroxyethyl)piperazino)pyrimidine;
2-Amino-5-(4-chlorophenoxy)-4-(4-(2-pivaloyloxyethyl)piperazino)pyrimidine;
2-Amino-4-(4-butyrylpiperazino)-5-(4-chlorophenoxy)pyrimidine;
2-Amino-5-(4-chlorophenoxy)-4-(4-phenoxyacetylpiperazino)pyrimidine;
2-Amino-4-(4-benzoylpiperazino)-5-(4-chlorophenoxy)pyrimidine;
2-Amino-5-(4-chlorophenoxy)-4-(4-(2-furoyl)piperazino)pyrimidine;
2-Amino-5-(4-chlorophenoxy)-4-(4-ethoxycarbonylpiperazino)pyrimidine;
2-Amino-5-(4-chlorophenoxy)-4-(4-phenoxycarbonylpiperazino)pyrimidine;
2-Amino-5-(4-chlorophenoxy)-4-(4-methoxydicarbonylpiperazino)pyrimidine;
2-Amino-4-(4-(3-carbamoylpropionyl)piperazino)-5-(4-chlorophenoxy)pyrimidine;
2-Amino-4-(4-(3-carboxypropionyl)piperazino)-5-(4-chlorophenoxy)pyrimidine;
2-Amino-5-(4-chlorophenoxy)-4-(4-(methylsulfonyl)piperazino)pyrimidine;
2-Amino-5-(4-chlorophenoxy)-4-(4-(phenylsulfonyl)piperazino)pyrimidine;
5-(4-Chlorophenoxy)-4-(4-methylpiperazino)-2-(1-pyrrolidinyl)pyrimidine;
2-(Anilino)-5-(4-chlorophenoxy)-4-(4-methylpiperazino)pyrimidine;
5-(4-Chlorophenoxy)-2-(4-fluoroanilino)-4-(4-methylpiperazino)pyrimidine;
2-(Benzylamino)-5-(4-chlorophenoxy)-4-(4-methylpiperazino)pyrimidine;
2,4-Bis(4-ethylpiperazino)-5-(4-chlorophenoxy)pyrimidine;
5-(4-(Chlorophenoxy)-4-(4-(2-hydroxyethyl)piperazino)-2-(isopropylamino)pyrimidine;
5-(4-Chlorophenoxy)-2-((2-hydroxyethyl)amino)-4-(4-(2-hydroxyethyl)piperazino)pyrimidine;
5-(4-Chlorophenoxy)-2-(2-(2-hydroxyethoxy)ethylamino)-4-(4-(2-hydroxyethyl)piperazino)pyrimidine;
2-(Anilino)-5-(4-chlorophenoxy)-4-(4-(2-hydroxyethyl)piperazino)pyrimidine;
5-(4-Chlorophenoxy)-2-(4-fluoroanilino)-4-(4-(2-hydroxyethyl)piperazino)pyrimidine;
5-(4-Chlorophenoxy)-4-(4-(2-hydroxyethyl)piperazino)-2-(4-methylanilino)pyrimidine;
5-(4-Chlorophenoxy)-4-(4-(2-hydroxyethyl)piperazino)-2-(1-pyrrolidinyl)pyrimidine;
5-(4-Chlorophenoxy)-4-(4-(2-hydroxyethyl)piperazino)-2-(piperidino)pyrimidine;
5-(4-Chlorophenoxy)-4-(4-(2-hydroxyethyl)piperazino)-2-(4-hydroxypiperidino)pyrimidine;
5-(4-Chlorophenoxy)-4-(4-(2-hydroxyethyl)piperazino)-2-(4-phenylpiperazino)pyrimidine;
5-(4-Chlorophenoxy)-4-(4-(2-hydroxyethyl)piperazino)-2-(4-methylpiperazino)pyrimidine;
5-(4-Chlorophenoxy)-2-(4-ethylpiperazino)-4-(4-(2-hydroxyethyl)piperazino)pyrimidine;

2,4-Bis(4-(2-hydroxyethyl)piperazino)-5-(4-chlorophenoxy)pyrimidine;

2-Chloro-5-(4-chlorophenoxy)-4-(4-(2-hydroxyethyl)piperazino)pyrimidine;

5-(4-Chlorophenoxy)-4-(4-(2-hydroxyethyl)piperazino)pyrimidine;

5-(4-Chlorophenoxy)-4-(4-methylpiperazino)pyrimidine;

2-Amino-5-(4-chlorophenoxy)-4-(4-hydroxypiperidino)pyrimidine;

2-Amino-4-(4-hydroxypiperidino)-5-(4-methylphenoxy)pyrimidine;

2-Amino-5-(2,4-dichlorophenoxy)-4-(4-hydroxypiperidino)pyrimidine;

5-(4-Chlorophenoxy)-4-(4-hydroxypiperidino)-2-morpholinopyrimidine;

2-Amino-5-(4-chlorophenoxy)-4-(3-(hydroxymethyl)piperidino)pyrimidine; and

2-Amino-5-(4-chlorophenoxy)-4-(2-(2-hydroxyethyl)piperidino)pyrimidine.

9. A pharmaceutical composition comprising a compound according to claim 1 and a pharmaceutically acceptable carrier therefor.

10. A pharmaceutical composition comprising a compound according to claim 8 and a pharmaceutically acceptable carrier therefor.

11. A method of enhancing the effect of nerve growth factor in a patient having need thereof, which comprises administering to said patient an effective amount of a compound of claim 1.

12. A method of enhancing the effect of nerve growth factor in a patient having need thereof, which comprises administering to said patient an effective amount of a compound of claim 8.

13. A method of enhancing the effect of nerve growth factor in a patient having need thereof, which comprises administering to said patient an effective amount of a compound of claim 4.

14. A method of enhancing the effect of nerve growth factor in a patient having need thereof, which comprises administering to said patient an effective amount of a compound of claim 5.

15. A method of enhancing the effect of nerve growth factor in a patient having need thereof, which comprises administering to said patient an effective amount of a compound of claim 6.

16. A method of enhancing the effect of nerve growth factor in a patient having need thereof, which comprises administering to said patient an effective amount of a compound of claim 7.

17. A method of treating a mammal having a neurodegenerative or neurological disorder of the central or peripheral nervous system which is responsive to the potentiation of nerve growth factor, comprising administering to said mammal a therapeutically effective amount of a compound of formula I according to claim 1, wherein the disorder is Alzheimer's disease.

18. A method of treating a mammal having a neurodegenerative or neurological disorder of the central or peripheral nervous system which is responsive to the potentiation of nerve growth factor, comprising administering to said mammal a therapeutically effective amount of a compound or formula I according to claim 1, wherein the disorder is peripheral neuropathy.

* * * * *

UNITED STATES PATENT AND TRADEMARK OFFICE
CERTIFICATE OF CORRECTION

PATENT NO. : 6,440,965 B1
DATED : August 27, 2002
INVENTOR(S) : Kelley et al.

It is certified that error appears in the above-identified patent and that said Letters Patent is hereby corrected as shown below:

Title page,
Item [22], PCT Filed,
"January 13, 1998" should read -- October 13, 1998 --.

Column 36,
Line 6, after "C6-10aryl" insert a comma (,) and a space.

Signed and Sealed this

Twenty-fourth Day of December, 2002

JAMES E. ROGAN
*Director of the United States Patent and Trademark Office*